(12) United States Patent
Hayashida et al.

(10) Patent No.: US 7,682,359 B2
(45) Date of Patent: Mar. 23, 2010

(54) HIGH-FREQUENCY TREATMENT APPARATUS

(75) Inventors: Tsuyoshi Hayashida, Sagamihara (JP); Kazunori Taniguchi, Hachioji (JP); Shigeo Nagayama, Hachioji (JP); Kazuya Hijii, Tama (JP)

(73) Assignee: Olympus Corporation, Tokyo (JP)

( * ) Notice: Subject to any disclaimer, the term of this patent is extended or adjusted under 35 U.S.C. 154(b) by 466 days.

(21) Appl. No.: 11/601,859

(22) Filed: Nov. 17, 2006

(65) Prior Publication Data
US 2007/0093812 A1   Apr. 26, 2007

Related U.S. Application Data

(63) Continuation of application No. PCT/JP2005/018421, filed on Oct. 5, 2005.

(30) Foreign Application Priority Data

Oct. 5, 2004 (JP) ............................ 2004-292956
Dec. 6, 2004 (JP) ............................ 2004-353425

(51) Int. Cl.
*A61B 18/12* (2006.01)

(52) U.S. Cl. .................................. 606/46; 49/1; 49/41

(58) Field of Classification Search .................. 606/37, 606/39, 45–50
See application file for complete search history.

(56) References Cited

U.S. PATENT DOCUMENTS

| | | | | |
|---|---|---|---|---|
| 5,007,907 A | * | 4/1991 | Nishigaki et al. | 606/46 |
| 5,178,606 A | * | 1/1993 | Ognier et al. | 604/31 |
| 5,486,173 A | * | 1/1996 | Vancaillie | 606/45 |
| 6,030,383 A | * | 2/2000 | Benderev | 606/45 |
| 6,494,881 B1 | * | 12/2002 | Bales et al. | 606/45 |
| 6,558,385 B1 | * | 5/2003 | McClurken et al. | 606/50 |
| 6,632,220 B1 | * | 10/2003 | Eggers et al. | 606/41 |
| 2004/0019351 A1 | | 1/2004 | Ohyama et al. | |
| 2004/0049251 A1 | * | 3/2004 | Knowlton | 607/101 |

FOREIGN PATENT DOCUMENTS

JP   2000-201946   7/2000

(Continued)

OTHER PUBLICATIONS

Machine Translation of JP 2003-230569 A.*

(Continued)

*Primary Examiner*—Michael Peffley
*Assistant Examiner*—Ronald Hupczey, Jr.
(74) *Attorney, Agent, or Firm*—Scully, Scott, Murphy & Presser, P.C.

(57) ABSTRACT

The present invention provides a high-frequency treatment apparatus including: an electrode assembly electrically connected to a high-frequency generating unit for generating a high-frequency current, the assembly having, at the distal end thereof, a current-applying electrode for discharging the high-frequency current, the proximal end of the current-applying electrode being covered with an insulator; an insertion section receiving the electrode assembly, the insertion section being located on the return side of the high-frequency current discharged from the current-applying electrode; a liquid supply section for supplying an irrigation liquid to the vicinity of the current-applying electrode; and an opening section provided at the distal end part of the insulator, the opening section supplying a gas to the vicinity of the current-applying electrode.

2 Claims, 24 Drawing Sheets

FOREIGN PATENT DOCUMENTS

| | | | | |
|---|---|---|---|---|
| JP | 2003-230569 | | | 7/2003 |
| JP | 2003230569 | A | * | 8/2003 |
| JP | 2003-265497 | | | 9/2003 |
| JP | 2003265497 | A | * | 9/2003 |
| JP | 2003-305055 | | | 10/2003 |
| JP | 2003305054 | A | * | 10/2003 |

OTHER PUBLICATIONS

Machine Translation of JP 2003-265497 A.*

Machine Translation of JP 2003-305054 A.*

* cited by examiner

HIGH-FREQUENCY TREATMENT APPARATUS

CROSS REFERENCES TO RELATED APPLICATION

This application is a continuation application of PCT/JP2005/018421 filed on Oct. 5, 2005 and claims benefit of Japanese Applications No. 2004-292956 filed in Japan on Oct. 5, 2004 and No. 2004-353425 filed in Japan on Dec. 6, 2004, the entire contents of each of which are incorporated herein by their reference.

BACKGROUND OF THE INVENTION

1. Field of the Invention

The present invention relates to a high-frequency treatment apparatus, used in an irrigation liquid, for performing electric surgery, such as resection, vaporization, or electric coagulation of body tissue.

2. Description of the Related Art

In the past resectoscope apparatuses have been included in high-frequency treatment apparatuses, used in an irrigation liquid, for performing electric surgery, such as resection, vaporization, or electric coagulation of body tissue.

A resectoscope apparatus, generally used for transurethral resection and transcervical resection, primarily includes an elongated hollow sheath to be inserted into the body cavity, a telescope, serving as an endoscope for observation, and an electrode unit for cauterization of body tissue, the telescope and electrode unit being disposed in the sheath.

During observing the body cavity using the resectoscope apparatus, a liquid is supplied through the sheath to the body cavity, thereby providing the field of vision of the endoscope.

In the past, as for the liquid supplied into the body cavity, D-Sorbitol, a nonconductive solution, has been used. A high-frequency current is supplied from an electrode to human body tissue and is then collected by a collector electrode arranged outside of the body.

In the conventional resectoscope apparatus, adductor contraction may be caused by stimulating a nerve through a high-frequency current. Accordingly, nerve block is needed. In addition, D-Sorbitol cannot be supplied into the body cavity for a long time. Unfortunately, time for surgical treatment is limited.

Japanese Unexamined Patent Application Publication No. 2000-201946 discloses a technique to overcome the above-described disadvantages. According to this technique, physiological saline is used as an irrigation liquid that can be supplied into the body cavity of a human being for a long time and a high-frequency current is collected by a sheath instead of a collector electrode, thus reducing nerve stimulation.

FIG. 30 is a diagram showing the structure of a conventional resectoscope apparatus using an irrigation liquid.

Referring to FIG. 30, a resectoscope apparatus 901 includes a resectoscope apparatus 902, a pack 903 of physiological saline, a liquid supply tube 904, a high-frequency power source 905, an electrode cable 906, and a footswitch 907.

A patient 909 lies on a surgical bed 908.

The distal end 911 of the resectoscope apparatus 902 is inserted into the urethra or the like of the patient 909. Referring to FIG. 31, the distal end 911 includes an electrode assembly 914 having an electrode 912 whose distal end part is shaped in a substantially semicircle. The electrode 912 of the electrode assembly 914 is covered with tube members 915 such that only the substantially semicircular distal end part is exposed.

Again referring to FIG. 30, the resectoscope apparatus 902 is supplied with physiological saline, serving as an irrigation liquid, from the pack 903 via the liquid supply tube 904. The resectoscope apparatus 902 is connected through the electrode cable 906 to the high-frequency power source 905.

When the footswitch 907 is pressed, the high-frequency power source 905 generates a high-frequency current and supplies the current through the electrode cable 906 to the electrode 912 arranged at the tip of the distal end 911 of the resectoscope apparatus 902.

FIG. 32 is a diagram explaining states of the vicinity of the electrode 912 when a high-frequency current is supplied to the electrode 912 at the distal end 911 of the above-described resectoscope apparatus 902.

As shown in FIG. 32, after starting of high-frequency current supply to the electrode 912 in an unenergized state, physiological saline is heated in the vicinity of the electrode 912 supplied with thermal energy through the electric impedance of the electrode 912, thus initiating the generation of bubbles 913.

The high-frequency current is further continuously supplied to the electrode 912, thus resulting in an increase of the amount of generated bubbles 913. Thus, the whole periphery of the electrode 912 is covered with the bubbles 913. At that time, the electrode impedance between the electrode 912 and the physiological saline steeply increases, so that a high voltage causes electric discharge. Resection, vaporization, or electric coagulation of body tissue can be achieved by heat generated by the electric discharge.

SUMMARY OF THE INVENTION

According to an aspect of the present invention, a high-frequency treatment apparatus includes: an electrode assembly electrically connected to a high-frequency generating unit for generating a high-frequency current, the assembly having, at the distal end thereof, a current-applying electrode for discharging the high-frequency current, the proximal end of the current-applying electrode being covered with an insulator; an insertion section receiving the electrode assembly, the insertion section being located on the return side of the high-frequency current discharged from the current-applying electrode; a liquid supply section for supplying an irrigation liquid to the vicinity of the current-applying electrode; and an opening section provided at the distal end part of the insulator, the opening section supplying a gas to the vicinity of the current-applying electrode.

The present invention realizes a high-frequency treatment apparatus capable of achieving resection, vaporization, and electric coagulation of body tissue in an irrigation liquid with less electric power and reducing time required for surgical treatment.

DESCRIPTION OF THE PREFERRED EMBODIMENTS

Embodiments of the present invention will now be described below with reference to the drawings.

First Embodiment

Figure 1:
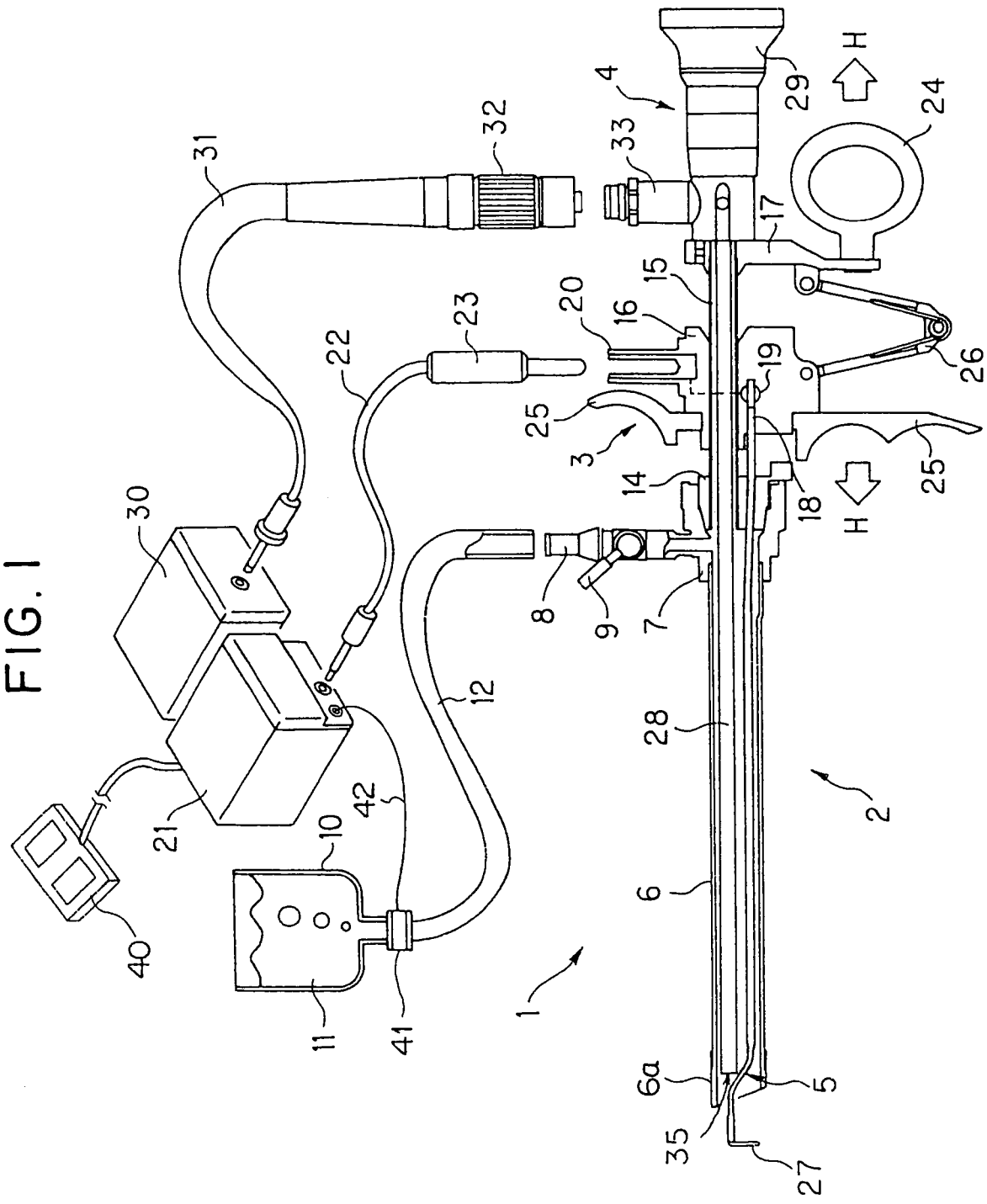
FIG. 1 is a diagram of the entire structure of a high-frequency treatment apparatus according to a first embodiment of the present invention.
Figure 2:
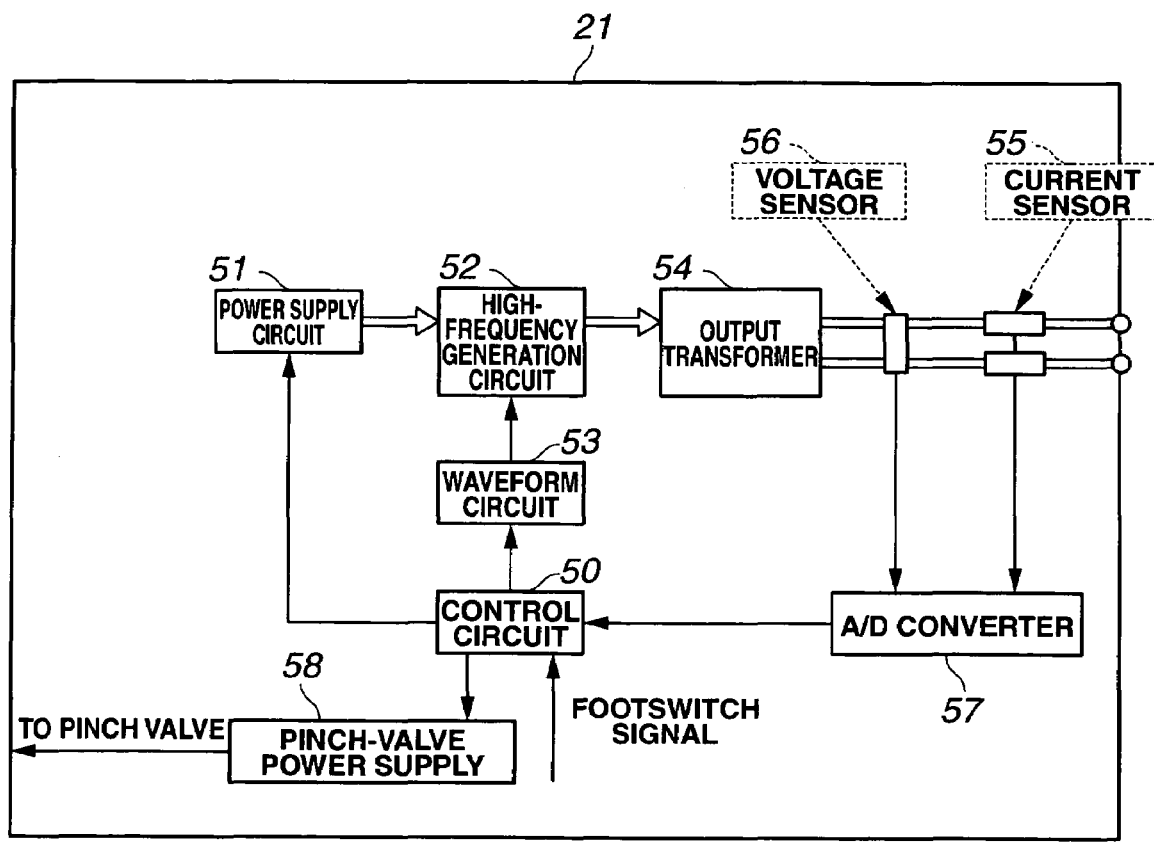
FIG. 2 is a block diagram of a high-frequency power supply unit according to the first embodiment.
Figure 3:
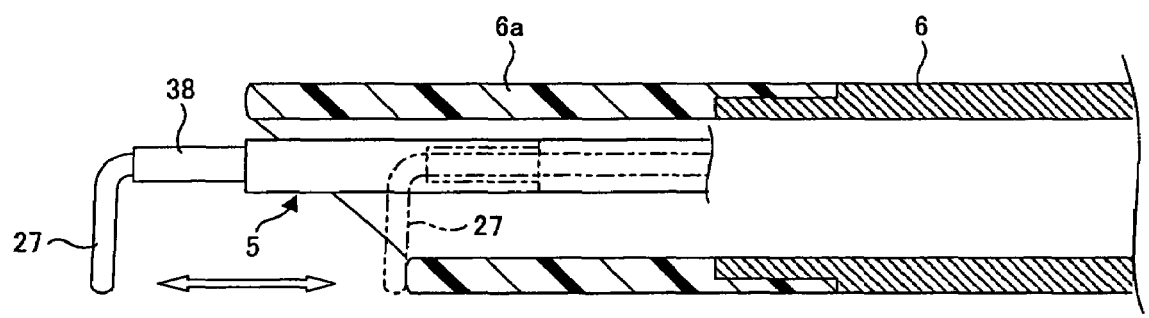
FIG. 3 is a sectional view showing distal end part of a resectoscope according to the first embodiment.
Figure 4:
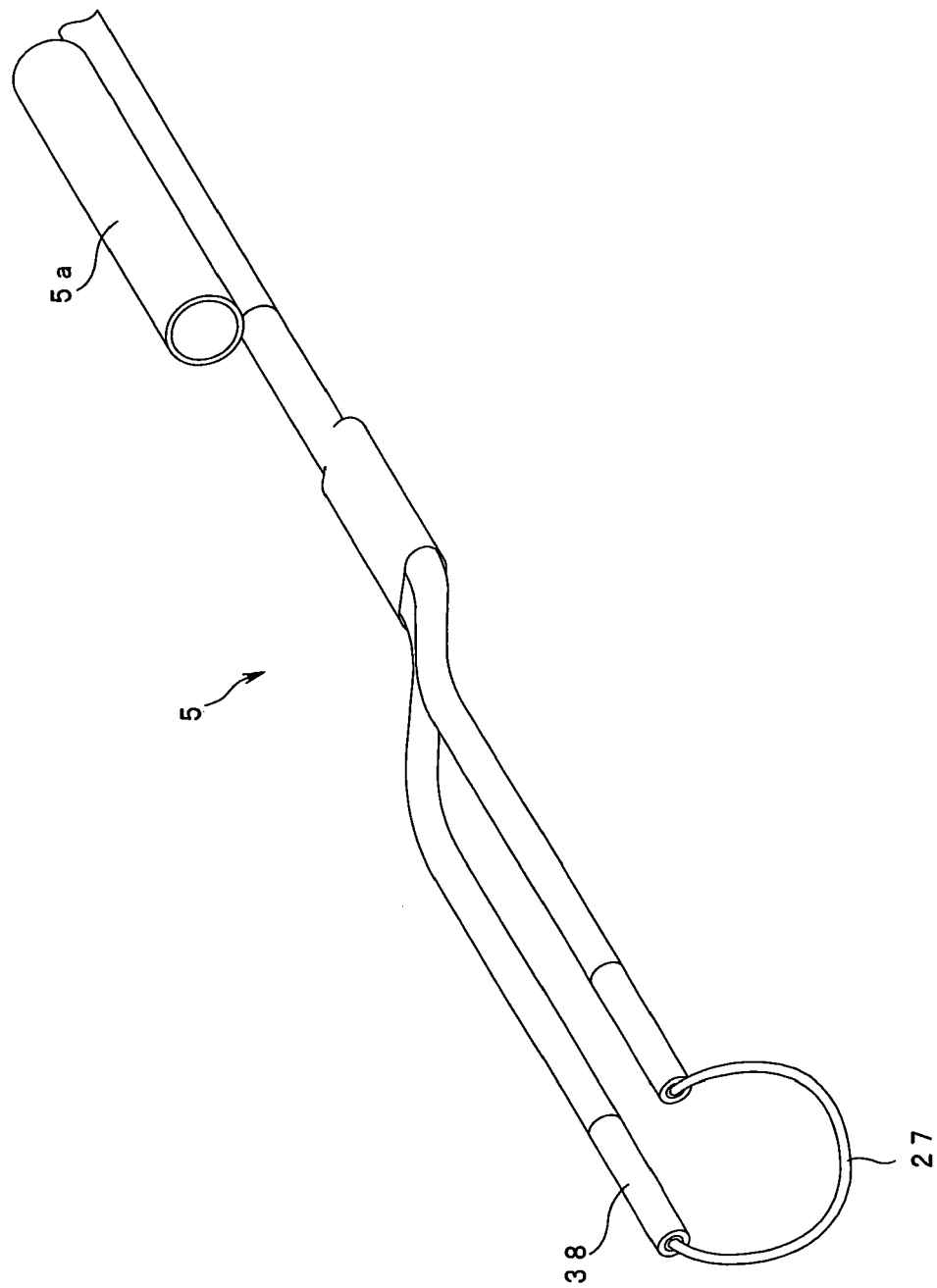
FIG. 4 is a diagram of the structure of an electrode assembly according to the first embodiment.
Figure 5:
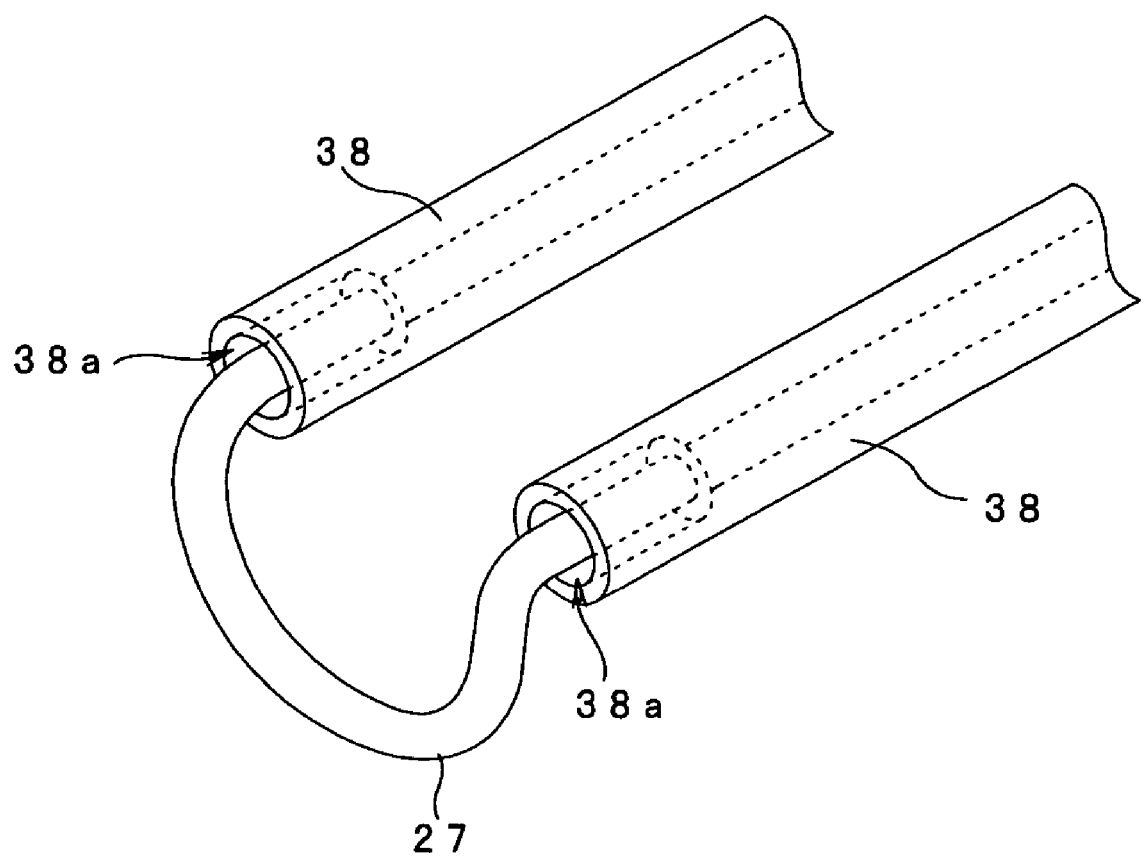
FIG. 5 is an enlarged view of distal end part of the electrode assembly.
Figure 6:
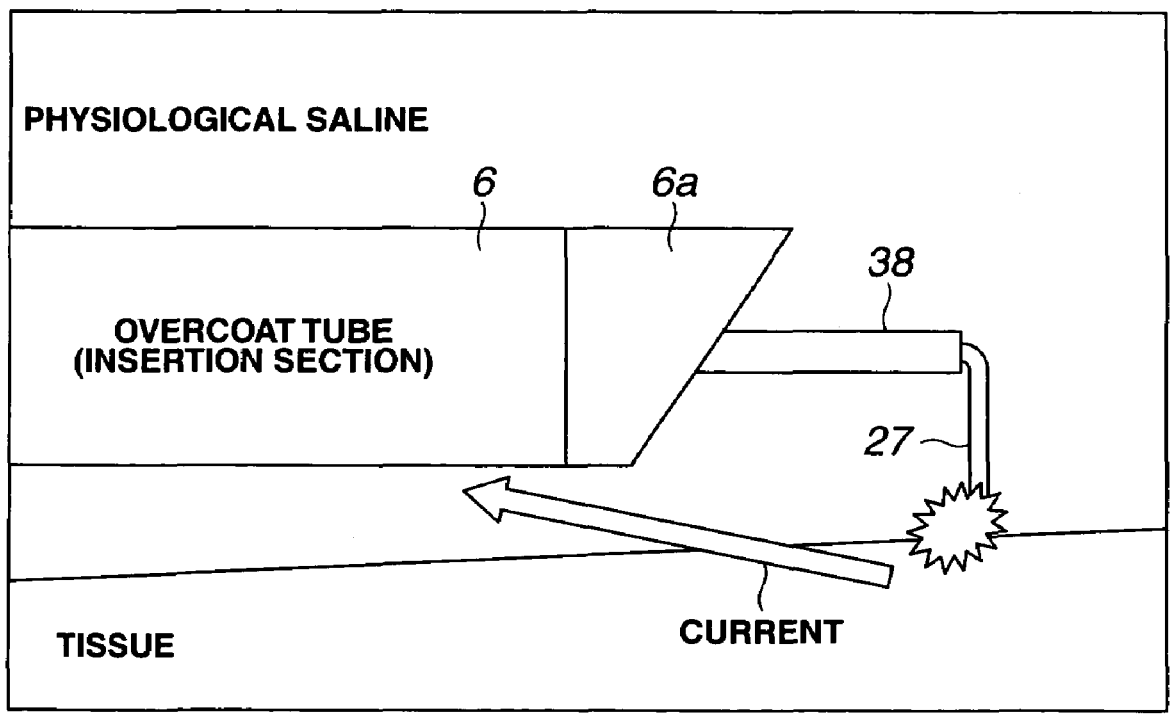
FIG. 6 is an enlarged view of the distal end part of the resectoscope to explain the operation thereof.
Figure 7:
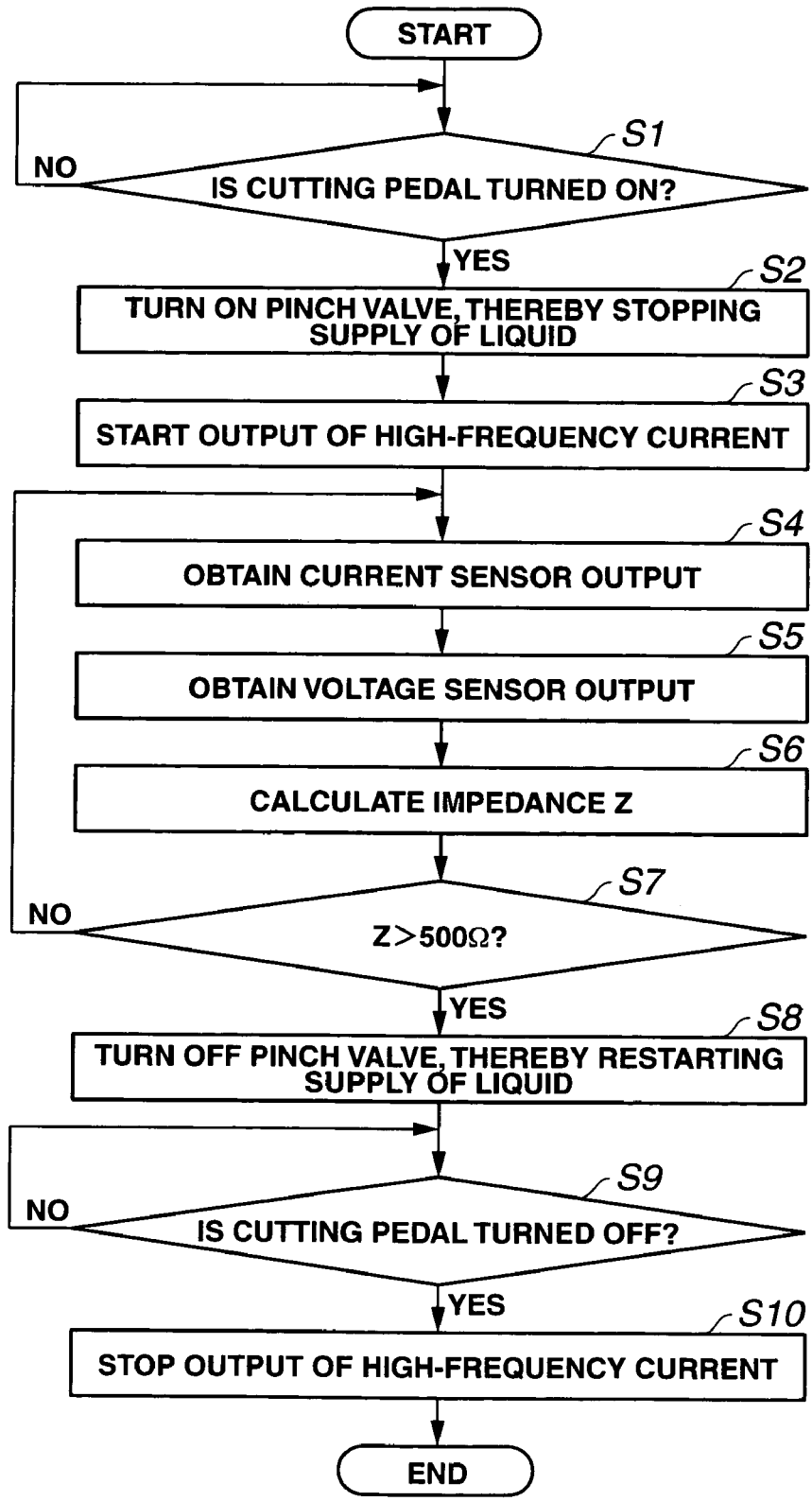
FIG. 7 is a flowchart showing control flow of the high-frequency power supply unit.

FIGS. 1 to 7 relate to a first embodiment of the present invention. FIG. 1 is a diagram of the entire structure of a high-frequency treatment apparatus. FIG. 2 is a block diagram of a high-frequency power supply unit. FIG. 3 is a sectional view showing distal end part of a resectoscope. FIG. 4 is a diagram of the structure of an electrode assembly. FIG. 5 is an enlarged view of distal end part of the electrode assembly. FIG. 6 is a flowchart showing control flow of the high-frequency power supply unit. FIG. 7 is an enlarged view of the distal end part of the resectoscope to explain the operation thereof.

Referring to FIG. 1, a resectoscope 1, serving as a high-frequency treatment apparatus, primarily includes a tubular sheath 2, an operation section 3 provided on the proximal end of the sheath 2, a telescope 4 which is inserted through the operation section 3 into the sheath 2 and is used for observation, a high-frequency power supply unit 21, serving as a high-frequency generating unit, and an electrode assembly 5 which is supplied with a high-frequency current from the high-frequency power supply unit 21 used for treatment of body tissue.

The sheath 2 is inserted into the body cavity of a subject through the urethra or vagina thereof. The sheath 2 includes a distal end portion 6a, a conductive insertion section 6, and a body 7 provided on the proximal end of the insertion section 6. The body 7 includes an outlet 8 through which physiological saline as an irrigation liquid is supplied to the body cavity via the insertion section 6, the outlet 8 being provided with a cock 9. The outlet 8 is designed such that a liquid supply tube 12 for supplying physiological saline 11 in a pack 10 is detachably connectable to the outlet 8.

On the other hand, the operation section 3 includes an operation-section body 14, a guide shaft 15, and a slider 16. The operation-section body 14 is detachable from the rear end of the body 7 of the sheath 2. The guide shaft 15 projects from the rear end of the operation-section body 14. The slider 16 is slidably supported by the guide shaft 15.

A stopper 17 is provided for the rear end of the guide shaft 15. The slider 16 is reciprocatable along the guide shaft 15 between the stopper 17 and the operation-section body 14. The guide shaft 15 is hollow. The telescope 4 is inserted into the sheath 2 through the guide shaft 15 and is detachably fixed to the stopper 17.

A holder 18 for holding the electrode assembly 5 is provided for the slider 16. In addition, an electrical connection unit 19 for supplying a high-frequency current to the electrode assembly 5 is provided for the slider 16. The electrical connection unit 19 is electrically connected to a connector 20 provided for the slider 16. An output plug 23 is arranged at the distal end of an output cord 22 of the high-frequency power supply unit 21. The output plug 23 is detachably fixable to the connector 20.

The high-frequency power supply unit 21 is connected to a footswitch 40 having selector pedals for controlling the operation of supplying a high-frequency current to the electrode assembly 5 and controlling the output level of high-frequency current. A signal cable 42 extends from the front surface of the high-frequency power supply unit 21 such that one end of the signal cable 42 is connected thereto. The other end of the signal cable 42 is connected to a pinch valve 41 which couples the pack 10 to the liquid supply tube 12. In other words, the pinch valve 41 is supplied with power through the signal cable 42 from the high-frequency power supply unit 21.

The pack 10, the liquid supply tube 12, and the pinch valve 41 constitute a liquid supply unit.

The stopper 17 includes a handle 24 into which a user's thumb is inserted. On the other, the slider 16 includes a handle 25 on which the user places their fingers, e.g., the index to ring or little fingers. The handles 24 and 25 are connected through a spring-loaded joint 26 such that they are biased by the spring-loaded joint 26 in the directions shown by arrows H.

When the handles 24 and 25 are operated to slide the slider 16 along the guide shaft 15 toward the operation-section body 14 (i.e., forwardly), a distal-end electrode 27 of the electrode assembly 5 is projected from the distal end of the sheath 2. On the other hand, when the slider 16 is moved toward the stopper (i.e., backwardly), the distal-end electrode 27 of the electrode assembly 5 is received in the distal end portion 6a of the sheath 2.

The telescope 4 includes an insertion section 28 inserted into the sheath 2 and an eyepiece 29 arranged at the rear end of the insertion section 28. A light guide connector 33 is arranged in the vicinity of the eyepiece 29. A connector 32 of a light guide cable 31 connected to a light source unit 30 is detachably fixable to the light guide connector 33.

Illumination light emitted from the light source unit 30 is transmitted through the light guide cable 31 to the light guide connector 33 and is further transmitted through a light guide bundle arranged in the insertion section 28 to the distal end 35 of the insertion section of the telescope 4, so that the light is released.

Referring to FIG. 2, the high-frequency power supply unit 21, serving as a high-frequency generating unit, includes a control circuit 50, a power supply circuit 51, a high-frequency generation circuit 52, a waveform circuit 53, an output transformer 54, a current sensor 55, a voltage sensor 56, an analog-to-digital (A/D) converter 57, and a pinch-valve power supply 58.

The power supply circuit 51 outputs a direct current. The high-frequency generation circuit 52 converts the direct current supplied from the power supply circuit 51 into a high-frequency current. The waveform circuit 53 designates the waveform of high-frequency current to the high-frequency generation circuit 52 under the control of the control circuit 50.

The output transformer 54 outputs the high-frequency current supplied from the high-frequency generation circuit 52 to wires in the output cord 22 connected to the resectoscope 1. The current sensor 55 detects an output current output from the output transformer 54.

The voltage sensor 56 detects an output voltage output from the output transformer 54. The A/D converter 57 converts signals output from the current sensor 55 and the voltage sensor 56 into digital signal data. The control circuit 50 controls the power supply circuit 51 and the waveform circuit 53 on the basis of the digital data supplied from the A/D converter 57 and a signal supplied from the footswitch 40. In addition, the control circuit 50 controls the pinch-valve power supply 58 for supplying power to the pinch valve 41.

The electrode assembly 5 to be projected from or received into the distal end portion 6a of the sheath 2 of the resectoscope 1 will now be described with reference to FIGS. 3 to 5.

Referring to FIG. 3, the distal-end electrode 27 of the electrode assembly 5 is exposed from the distal end portion 6a of the resectoscope 1. The distal-end electrode 27 is bent in a substantially L-shape as viewed from the side so that the distal-end electrode 27 is easily contactable with the body tissue. As mentioned above, the electrode assembly 5 is slidable in such a manner that when the handles 24 and 25 (see FIG. 1) are operated, the distal end part including the distal-end electrode 27 is projected forward from the distal end portion 6a of the resectoscope 1, alternatively, the distal end part is substantially received into the distal end portion 6a.

Referring to FIG. 4, the electrode assembly 5 has a longitudinal axis along the sheath 2. The distal end part of the electrode assembly 5 is branched into two segments. The distal-end electrode 27, serving as a current-applying electrode made of a metal wire shaped in a substantially loop, is arranged such as to interconnect ends of the two branched segments. A sleeve 38, serving as an electrical insulating member, is arranged on the distal end of each branched segment of the electrode assembly 5.

A guide tube 5a is fixed to an upper portion, as viewed in FIG. 4, of the distal-end electrode 27 such that the guide tube 5a is positioned between the branch point of the electrode assembly 5 and the proximal end. The insertion section 28 of the telescope 4 is inserted through the guide tube 5a. Accordingly, when being slid, the electrode assembly 5 is guided straight by the guide tube 5a through which the insertion section 28 of the telescope 4 is inserted.

Referring to FIG. 5, a hole 38a having a space with an opening at the distal end face is formed at the distal end of each sleeve 38. The diameter of the hole 38a in each sleeve 38 is larger than the outer diameter of the distal-end electrode 27 such that a predetermined gap (space) is formed between the inner surface of the sleeve 38 and the outer surface of the distal-end electrode 27. The hole 38a has a predetermined length toward the proximal side of the sleeve 38.

In other words, the two sleeves 38 cover base parts of the distal-end electrode 27 made of a metal wire shaped in a substantially loop, respectively. The base parts are loosely fitted into the respective holes 38a at the distal ends of the two sleeves 38. The base parts extending from the respective openings of the holes 38a are bent downwardly, i.e., vertically in a substantially L-shape as viewed from the side.

The operation of the resectoscope 1 with the above-described structure according to the present embodiment will now be described below with reference to FIGS. 6 and 7. The control circuit 50 of the resectoscope 1 performs the control operation in accordance with a routine including steps (S) of a flowchart in FIG. 7.

First, the resectoscope 1 is inserted into the body cavity of a patient through, e.g., the urethra or vagina thereof.

When a foot pedal of the footswitch 40 is pressed, i.e., turned on (S1), as shown in FIG. 6, the control circuit 50 controls the pinch-valve power supply 58 to supply power to the pinch valve 41, thereby temporarily interrupting the supply of physiological saline through the liquid supply tube 12 (S2). The control circuit 50 controls the high-frequency generation circuit 52 to start the supply of a high-frequency current (S3).

At that time, since the supply of physiological saline is stopped, physiological saline heated by the high-frequency current is remained in the vicinity of the distal-end electrode 27, so that bubbles are easily generated. In addition, the generated bubbles are not scattered by supplying the liquid. As shown in FIG. 6, the high-frequency current, supplied to the distal-end electrode 27, flows from an area (treatment region), where the distal-end electrode 27 as a current-applying electrode is in contact with body tissue, to the insertion section 6 located on the return side. Consequently, the body tissue in contact with the distal-end electrode 27 is subjected to resection, vaporization, or electric coagulation.

Heat energy is transferred from the distal-end electrode 27 in the holes 38a to physiological saline in the holes 38a at the distal ends of the respective sleeves 38, so that the temperature of physiological saline in the holes 38a is increased to the temperature, at which bubbles are generated, in a short time. Accordingly, bubbles are easily generated on the periphery of the distal-end electrode 27 in the vicinity of the distal ends of the respective sleeves 38. Therefore, the whole periphery of the distal-end electrode 27 can be covered with generated bubbles in a short period of time. Thus, the high-frequency current supplied to the distal-end electrode 27 is efficiently discharged from the area where the distal-end electrode 27 is in contact with the body tissue to the insertion section 6.

After that, the control circuit 50 acquires a current value of the current sensor 55 through the A/D converter 57 in step S4 and then obtains a voltage value of the voltage sensor 56 therethrough in step S5.

The control circuit 50 divides the obtained voltage value by the obtained current value to obtain an impedance value Z between the distal-end electrode 27 and the insertion section 6, serving as an overcoat tube (S6).

Next, the control circuit 50 then determines whether the calculated impedance value Z is less than, e.g., 500Ω (S7). If the impedance value Z is less than 500Ω, the process is returned to step S4 and the control circuit 50 repeats step 4 and the subsequent steps.

On the other hand, if the calculated impedance value Z is larger than 500Ω, this means that the whole periphery of the distal-end electrode 27 is covered with bubbles because electric discharge has already been generated. It is not necessary to interrupt the supply of physiological saline. The control circuit 50 turns off the power supply to the pinch valve 41, thereby restarting the supply of physiological saline to the vicinity of the distal-end electrode 27 (S8).

When the foot pedal of the footswitch 40 is released (turned off) (S9), the control circuit 50 controls the high-frequency generation circuit 52 to stop the output of high-frequency current (S10).

In other words, as mentioned above, when the foot pedal of the footswitch 40 is turned on, bubbles are generated on the distal-end electrode 27. However, just after the foot pedal of the footswitch 40 is turned on, bubbles are poorly generated on the distal-end electrode 27 because it takes time to increase the temperature of physiological saline. At that time, the impedance value Z of tissue impedance is lower than 500Ω. The control circuit 50 turns on the power supply to the pinch valve 41 and interrupts the supply of physiological saline to the vicinity of the distal-end electrode 27 through the liquid supply tube 12.

After a predetermined lapse of time from the turn-on of the foot pedal of the footswitch 40, the amount of bubbles on the distal-end electrode 27 is increased, thus resulting in an increase in the impedance value Z. When the impedance value Z equals 500Ω, the whole periphery of the distal-end electrode 27 is covered with bubbles, electric discharge is generated, the power supply to the pinch valve 41 is turned off, and the supply of physiological saline to the vicinity of the distal-end electrode 27 through the liquid supply tube 12 is restarted.

Figure 30:
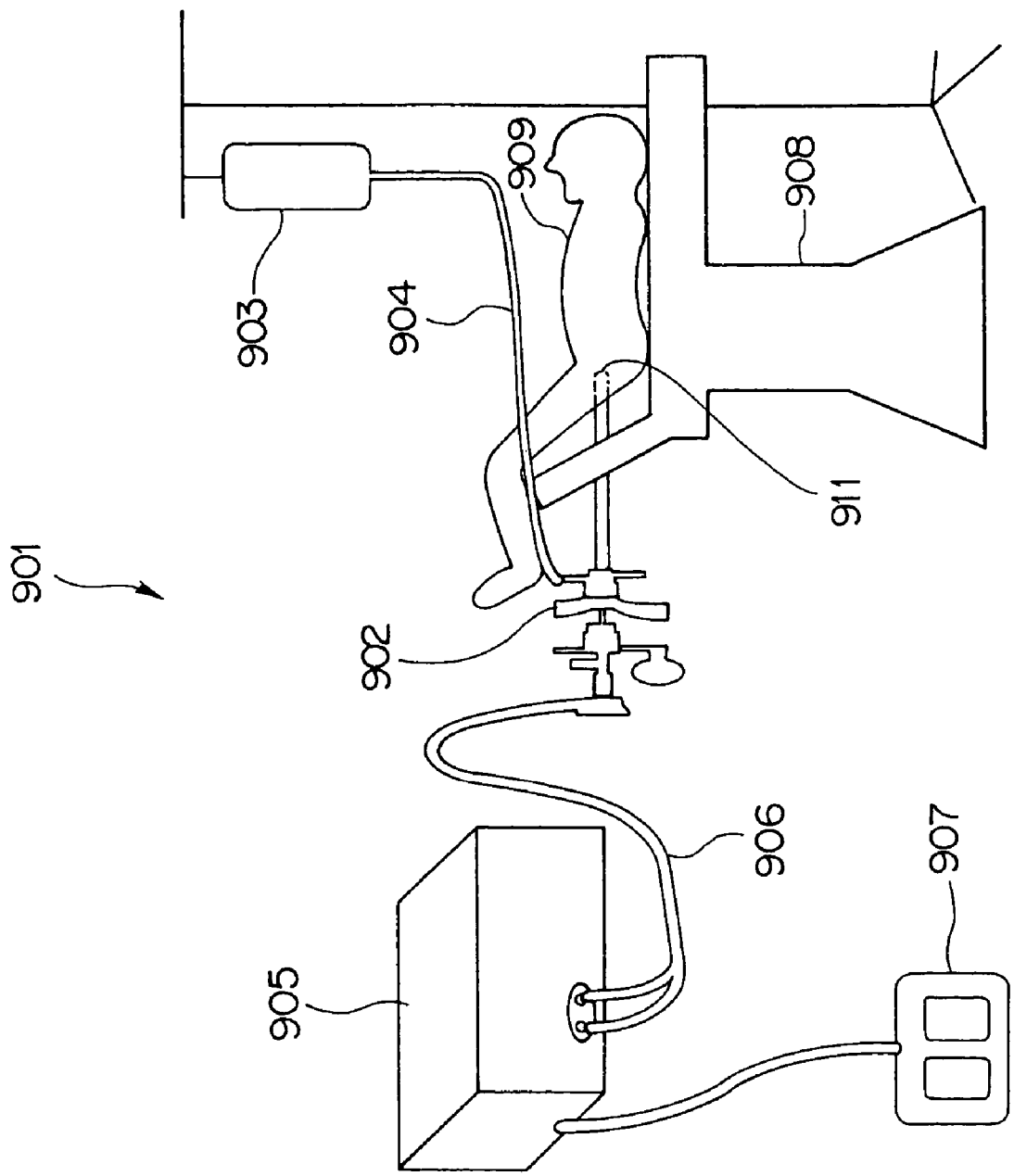
FIG. 30 is a diagram showing the structure of a high-frequency treatment apparatus including a conventional resectoscope using an irrigation liquid, such as physiological saline.
Figure 31:
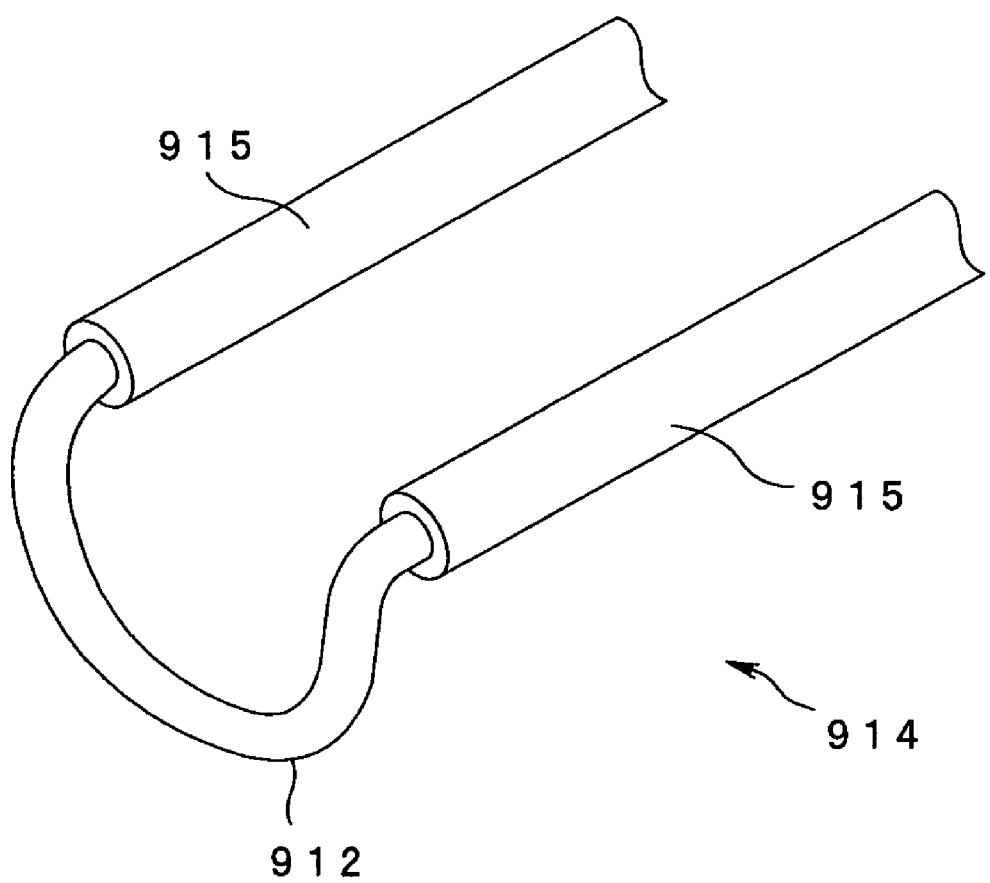
FIG. 31 is a diagram showing a conventional electrode.
Figure 32:
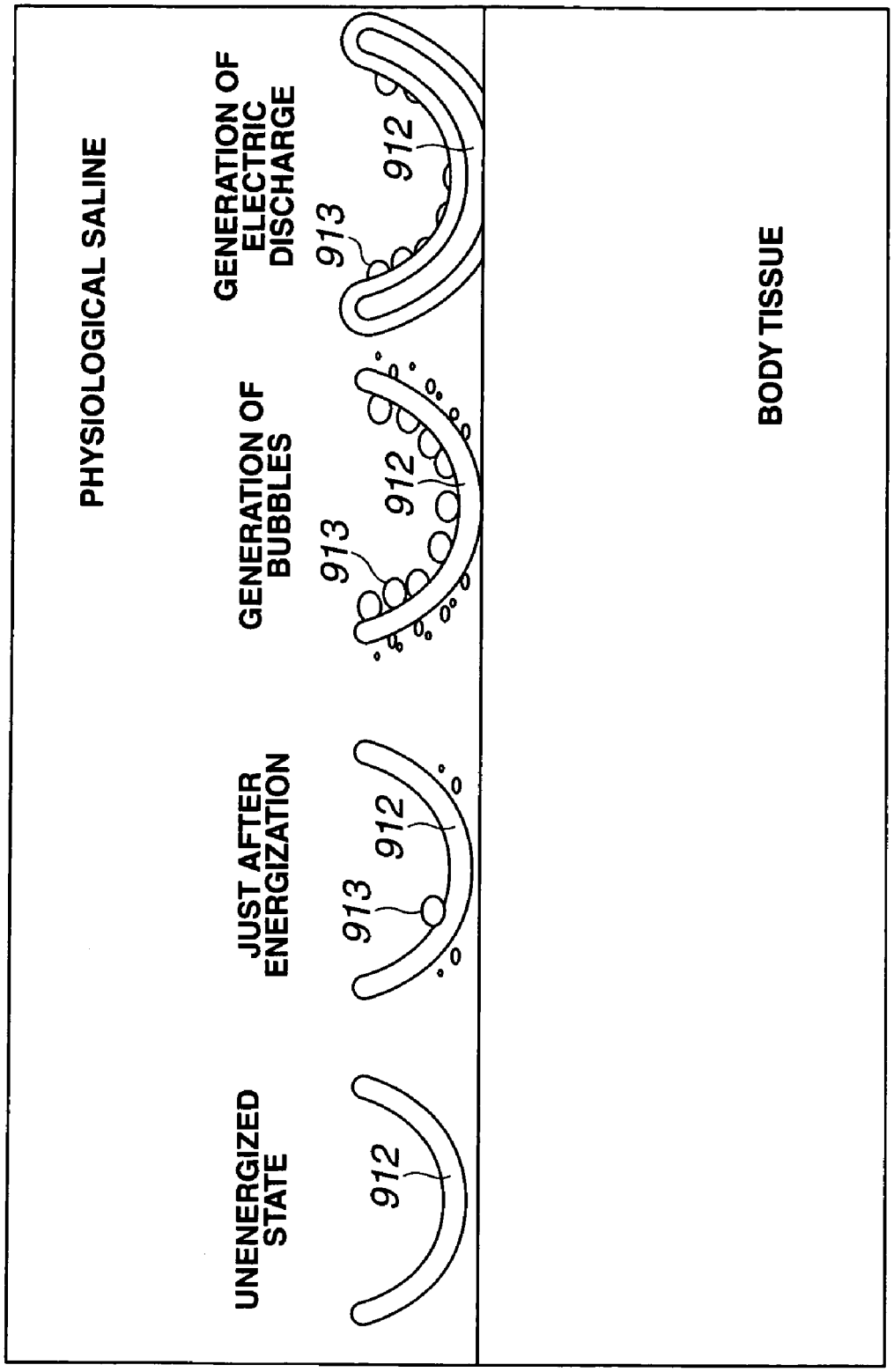
FIG. 32 is a diagram explaining states of the vicinity of the electrode of the conventional resectoscope.

According to the present embodiment, as compared with the electrode 912 provided for the conventional resectoscope apparatus 901 shown in FIGS. 30 to 32, bubbles are generated in the holes 38a in the respective sleeves 38 in a short time, thus increasing the amount of generated bubbles to cover the whole periphery of the distal-end electrode 27 for electric discharge. In other words, the resectoscope 1 according to the present embodiment is designed so as to reduce the time required to generate bubbles to cover the whole periphery of the distal-end electrode 27 after the turn-on of the foot pedal of the footswitch 40.

In the resectoscope 1 with the above-described structure according to the present embodiment, the time required to cover the whole periphery of the distal-end electrode 27 with bubbles after starting of high-frequency current output by the high-frequency power supply unit 21 can be reduced, the covering with bubbles being needed to generate electric discharge between the distal-end electrode 27 and the insertion section 6. In other words, since the temperature of physiological saline in the holes 38a of the respective sleeves 38 is raised quickly, the time required to increase the temperature of physiological saline necessary to generate bubbles to cover the periphery of the distal-end electrode 27 can be reduced.

Advantageously, in the resectoscope 1 according to the present embodiment, electric power saving effect can be obtained by reducing the time during which the high-frequency power supply unit 21 outputs a high-frequency current. In addition, bubbles to cover the whole periphery of the distal-end electrode 27 can be easily generated.

Further, since bubbles in the vicinity of the distal-end electrode 27 are not scattered due to the supply of liquid, the whole of the distal-end electrode 27 is covered with bubbles to generate electric discharge by low electric power, so that resection, vaporization, or electric coagulation of body tissue can be achieved.

Consequently, the high-frequency power supply unit 21 with low electric power can be used. Thus, a reduction in manufacturing cost of the resectoscope 1, serving as a high-frequency treatment apparatus, can be reduced and electric power can be saved.

Figure 8:
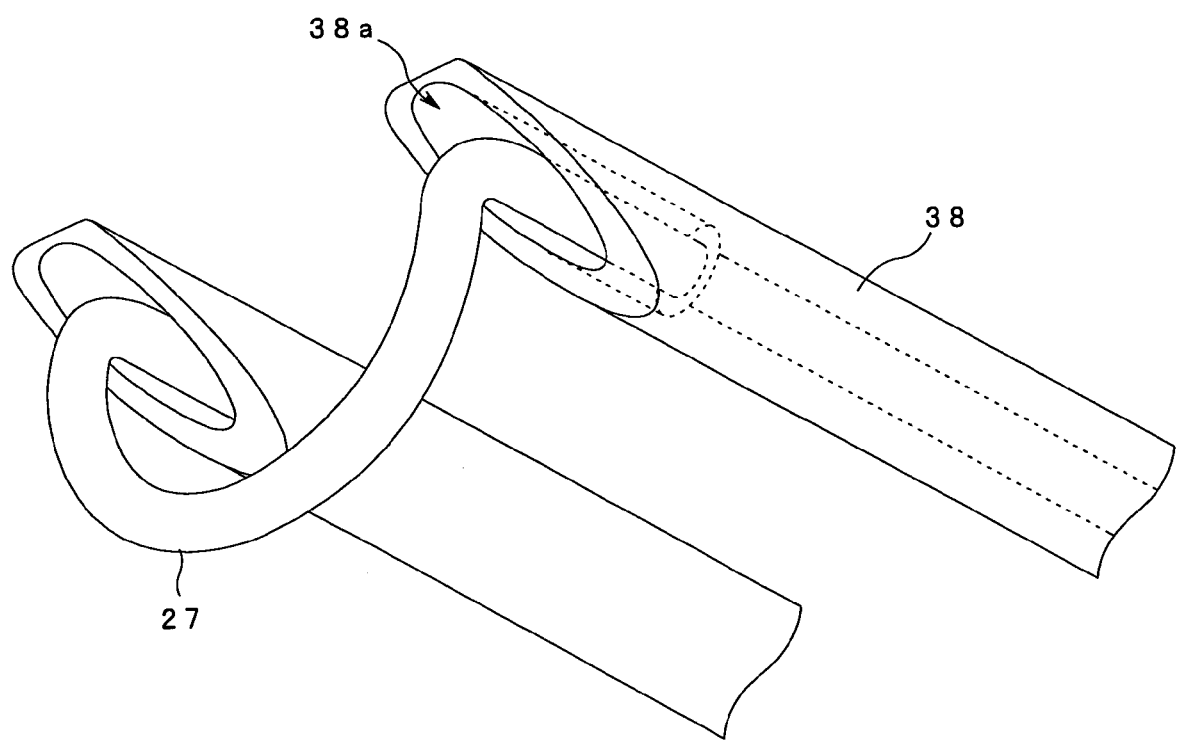
FIG. 8 is an enlarged view of distal end part of an electrode assembly according to a modification of the first embodiment.

Referring to FIG. 8, the distal end of each sleeve 38 may be cut at an angle such that the upper edge extends forward over the lower edge as viewed from the side, each sleeve 38 including a hole 38a into which the distal-end electrode 27 is loosely fitted. In other words, the sleeve 38 is beveled at a predetermined angle in the direction along the axis thereof such that the upper edge extends forward over the lower edge as viewed in the direction perpendicular to the vertical direction in the figure. In other words, a flange constituting a retaining mechanism is formed at the distal end of each sleeve 38.

Accordingly, the upper edge of the distal end of each sleeve 38 makes bubbles generated in the hole 38a hard to move upward in physiological saline. Advantageously, the whole periphery of the distal-end electrode 27 is efficiently covered with bubbles.

In the above-described resectoscope 1 according to the present embodiment, since electric discharge is effectively generated between the distal-end electrode 27 and the insertion section 6 by a small amount of generated bubbles while the distal-end electrode 27 is being in contact with body tissue, the power consumption of the high-frequency power supply unit 21 can be reduced and high-frequency electric power to be used can be realized with a small amount of power. Accordingly, an expensive high-frequency power supply unit 21 capable of outputting a large amount of power is not needed. An inexpensive high-frequency power supply unit 21 capable of immediately generating electric discharge between the distal-end electrode 27 and the insertion section 6 by a small amount of power while the distal-end electrode 27 is in contact with body tissue can be used.

In the resectoscope 1 according to the present embodiment, since the time required to generate electric discharge can be reduced, the time required for surgical treatment can be reduced. Advantageously, burdens on the patient can also be reduced.

Second Embodiment

A second embodiment will now be described below with reference to FIGS. 9 to 14.

Figure 9:
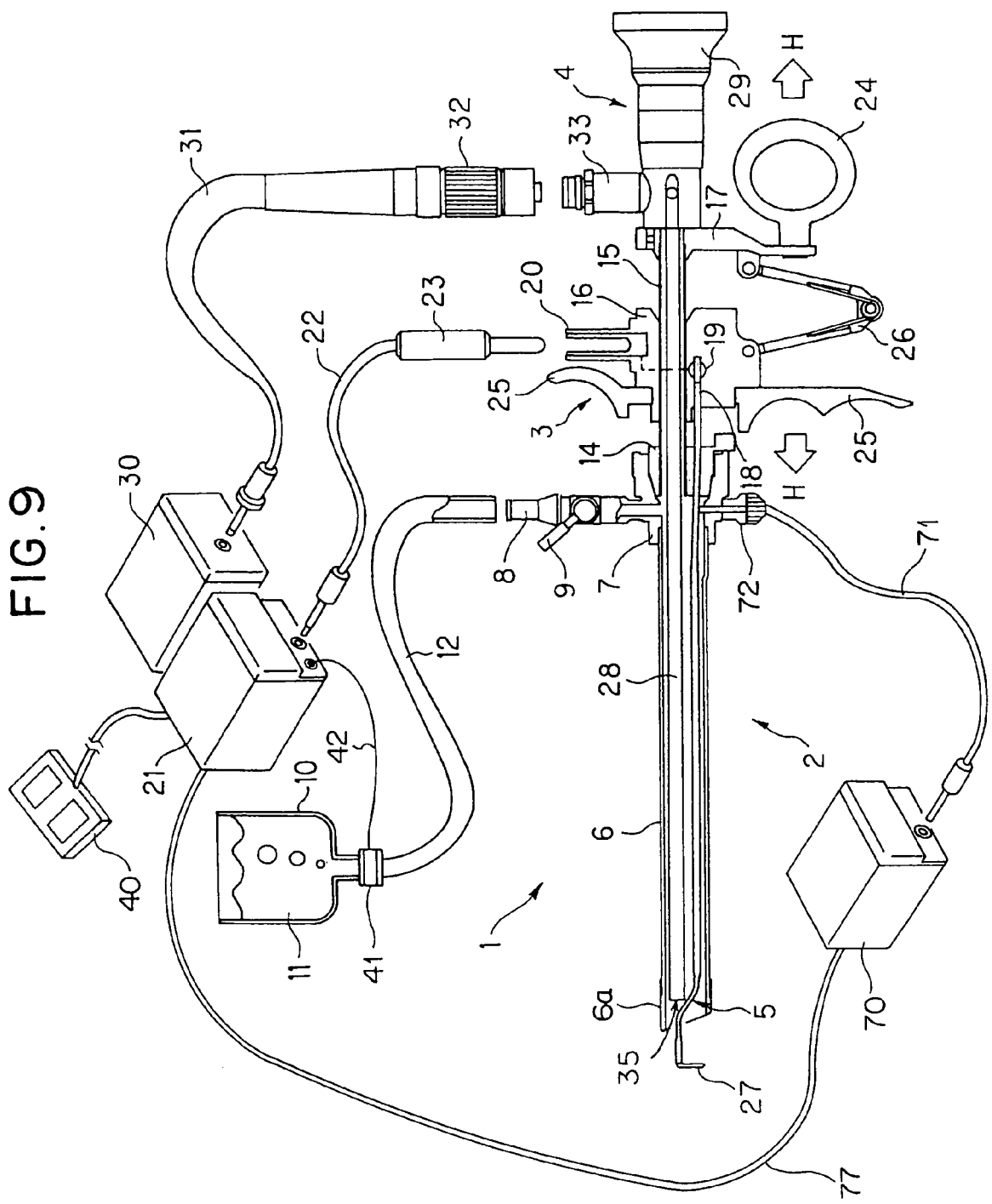
FIG. 9 is a diagram of the entire structure of a high-frequency treatment apparatus according to a second embodiment.

FIGS. 9 to 14 relate the second embodiment of the present invention. FIG. 9 is a diagram of the entire structure of a high-frequency treatment apparatus. FIGS. 10 to 14 are enlarged view of distal end part of an electrode assembly.

In the description of the present embodiment, the same components as those of the first embodiment are designated by the same reference numerals and a description of the previously described components is omitted.

Referring to FIG. 9, a resectoscope 1, serving as a high-frequency treatment apparatus according to the present embodiment, includes a gas supply connector 72 that is arranged on a body 7 of a sheath 2. A gas supply tube 71 extends from the gas supply connector 72 such that one end of the gas supply tube 71 is connected thereto. The other end of the gas supply tube 71 is connected to a gas supply unit 70, serving as a gas supply unit.

The gas supply unit 70 is connected to a footswitch 40 through a high-frequency power supply unit 21 by an electric cable 77. When a gas-supply foot pedal of the footswitch 40 is turned on, a gas supply pump built in the gas supply unit 70 is driven under the control of the high-frequency power supply unit 21. The gas supply unit 70 may be connected to another operating switch different from the footswitch 40.

A gas supply passage is formed in the gas supply connector 72 and the body 7 and is connected to an intermediate portion of an electrode assembly 5. In other words, a gas output from the gas supply unit 70, e.g., air in the present embodiment, is supplied into the electrode assembly 5 through the gas supply tube 71.

Figure 10:
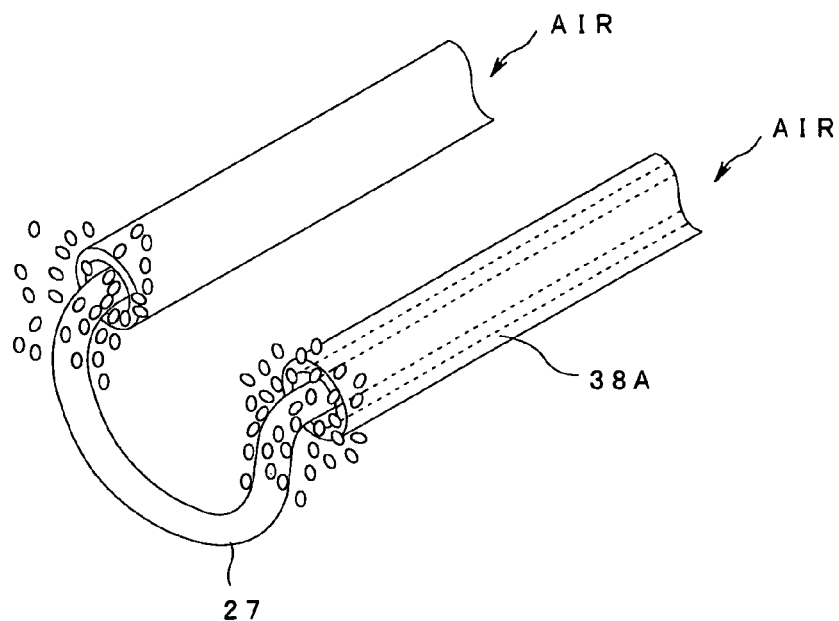
FIG. 10 is an enlarged view of distal end part of an electrode assembly according to the second embodiment.

Referring to FIG. 10, distal end part of the electrode assembly 5 is designed such that the inner surface of each sleeve 38A covering a distal-end electrode 27 is not in tight contact with the outer surface of the proximal end of associated base part of the distal-end electrode 27 so as to expel air from the distal end of the sleeve 38A, the air being supplied into the electrode assembly 5. In other words, each sleeve 38A is a tube having an inner diameter larger than the outer diameter of the distal-end electrode 27. The base parts of the distal-end electrode 27 are loosely fitted into the sleeves 38A, serving as tubes.

Therefore, air supplied into the electrode assembly 5 is allowed to flow toward the distal end of the electrode assembly 5 and is then expelled from openings at the distal ends of the respective sleeves 38A. Accordingly, while the resectoscope 1 is inserted into the body cavity of a patient and physiological saline is supplied to the vicinity of the distal-end electrode 27, the whole periphery of the distal-end electrode 27 is covered with bubbles of air expelled from the openings at the distal ends of the sleeves 38A and bubbles generated by increasing the temperature of physiological saline.

In other words, even when the amount of bubbles generated by increasing the temperature of physiological saline is small, bubbles to cover the whole periphery of the distal-end electrode 27 can be generated in a short time by air expelled from the openings at the distal ends of the sleeves 38A, the covering of the distal-end electrode 27 with bubbles being needed to generate electric discharge for surgical treatment of body tissue. Thus, electric discharge to the insertion-section 6 from the distal-end electrode 27 in contact with body tissue in a treatment region can be easily generated.

According to the present embodiment, since bubbles to cover the whole periphery of the distal-end electrode 27 are generated within a shorter time period by air forcedly expelled from the openings at the distal ends of the sleeves 38A as compared to the electrode 912 provided for the conventional resectoscope apparatus 901 shown in FIGS. 30 to 32, electric discharge to the insertion section 6 from the distal-end electrode 27 in contact with body tissue can be immediately generated. In other words, the resectoscope 1 according to the present embodiment has such a structure that the time required to generate bubbles to cover the whole periphery of the distal-end electrode 27 after the turn-on of a cutting pedal of the footswitch 40 can be reduced and resection, vaporization, and electric coagulation of body tissue can be performed.

Figure 11:
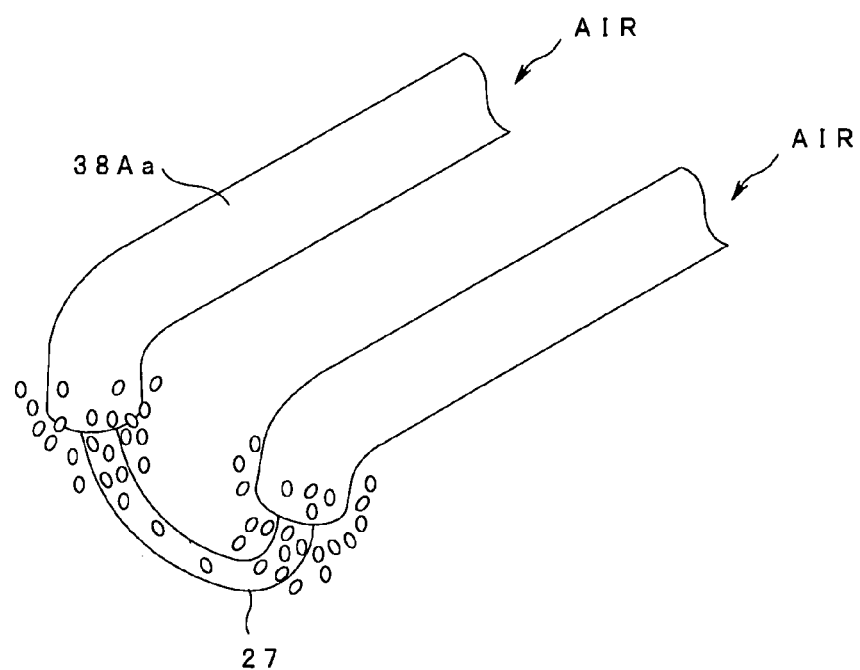
FIG. 11 is an enlarged view of distal end part of an electrode assembly according to a modification of the second embodiment.
Figure 12:
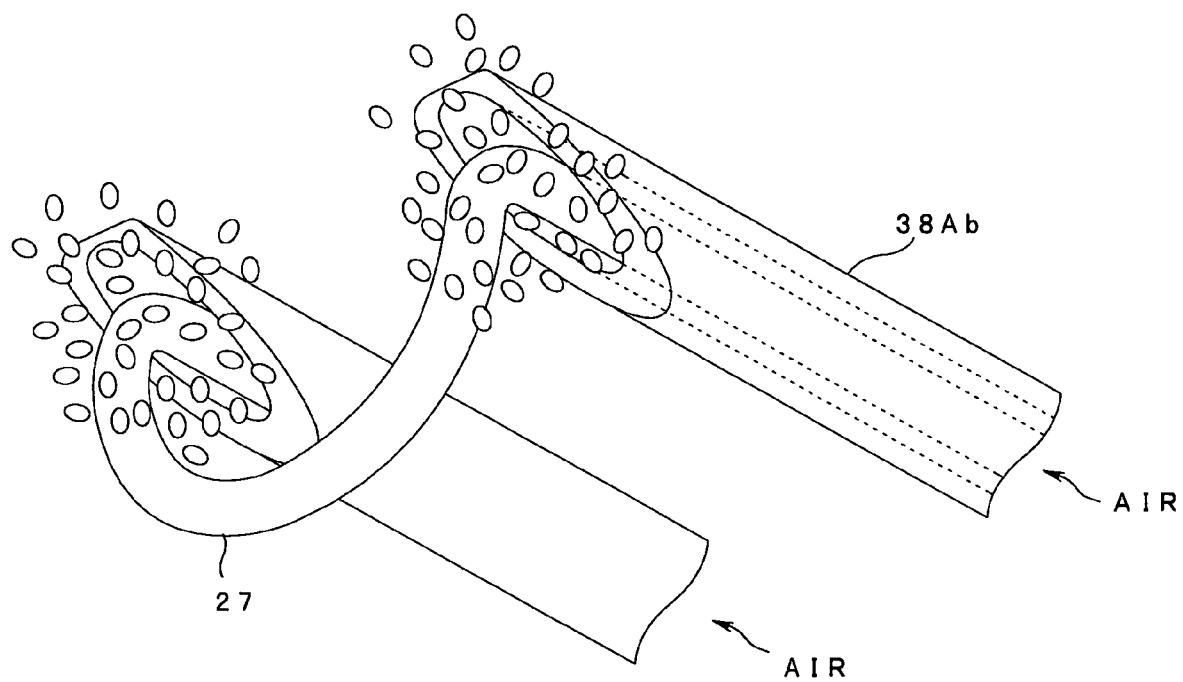
FIG. 12 is an enlarged view of distal end part of an electrode assembly according to another modification.
Figure 13:
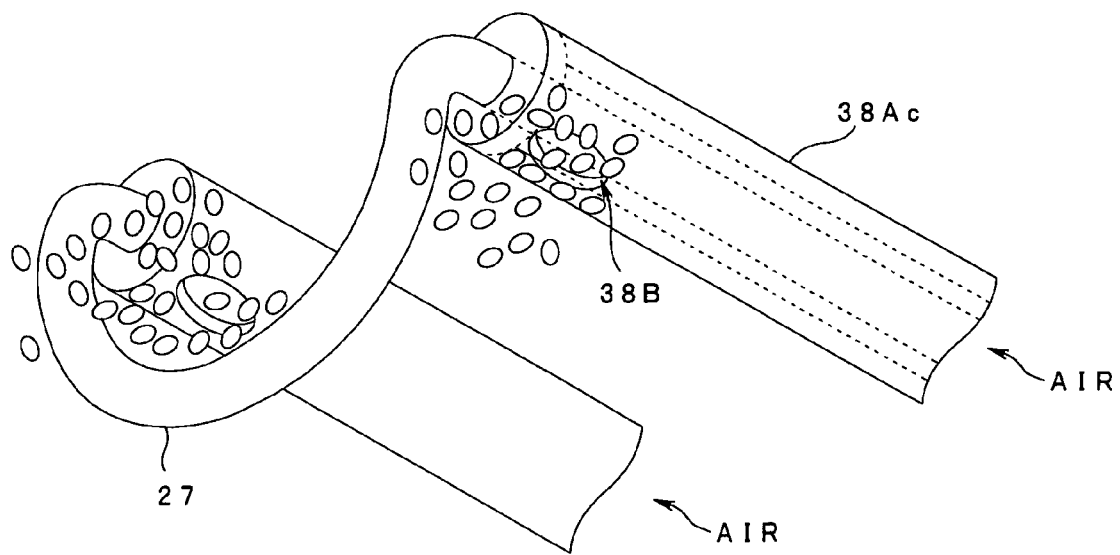
FIG. 13 is an enlarged view of distal end part of an electrode assembly according to another modification.
Figure 14:
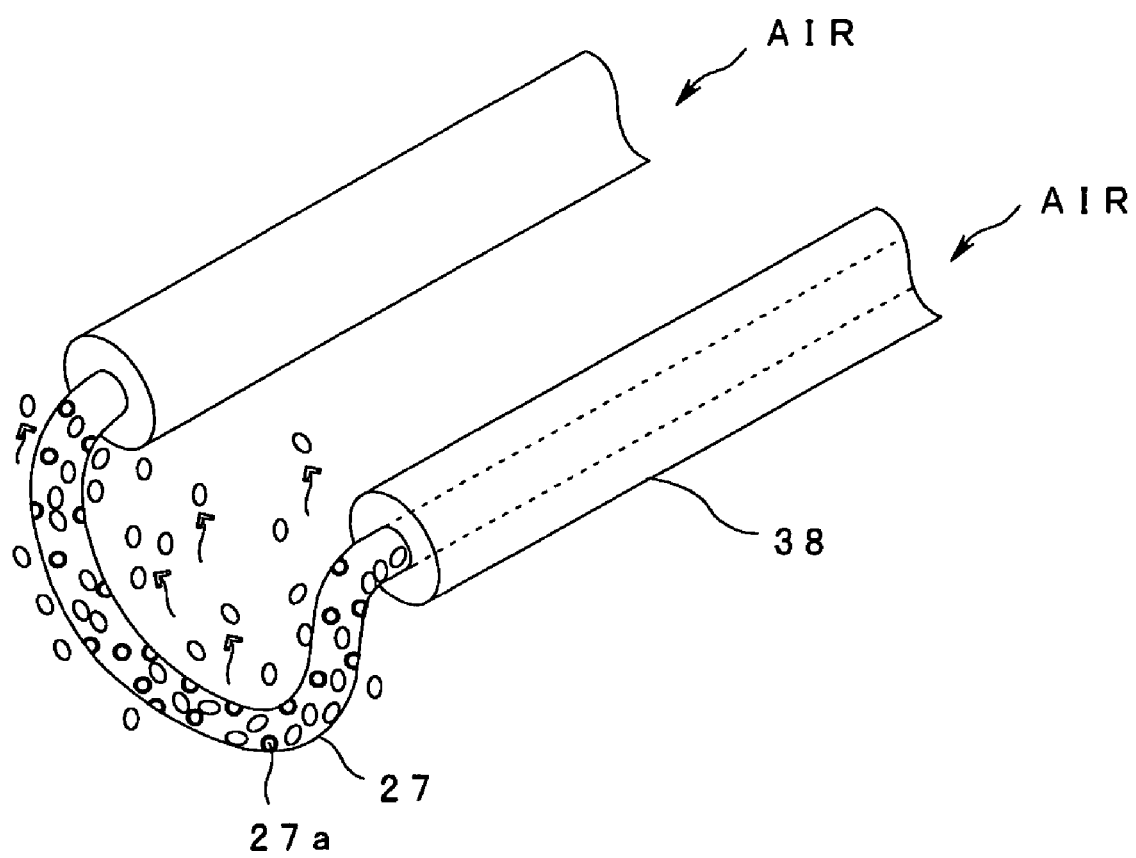
FIG. 14 is an enlarged view of distal end part of an electrode assembly according to another modification.

Each sleeve covering the associated base part of the distal-end electrode 27 may be designed as shown in FIGS. 11 to 13, which will be described below in detail. The distal-end electrode 27 may be designed as shown in FIG. 14.

Referring to FIG. 11, a sleeve 38Aa may extend downwardly in a substantially L-shape as viewed from the side, i.e., vertically as viewed in the drawing, such that the sleeve extends along the distal-end electrode 27 that is bent downwardly. Thus, air to be expelled from openings at the distal ends of the sleeves 38Aa is ejected along the distal-end electrode 27. Advantageously, bubbles to cover the whole periphery of the distal-end electrode 27 can be efficiently generated in a short time.

Referring to FIG. 12, the distal end of each sleeve 38Ab is cut at a bevel such that the upper edge extends forward over the lower edge as viewed from the side. In other words, each sleeve 38Ab is beveled at a predetermined angle in the axial direction such that the upper edge extends forward over the lower edge as viewed in the direction perpendicular to the vertical direction. In other words, a flange constituting a retaining mechanism is formed at the distal end of each sleeve 38Ab.

Accordingly, the upper edge of the distal end of each sleeve 38Ab makes bubbles expelled therefrom hard to move upward in physiological saline. Advantageously, the whole periphery of the distal-end electrode 27 is efficiently covered with bubbles.

Referring to FIG. 13, the distal end of each sleeve 38Ac is formed in such a manner that an inner duct is sealed at the distal end surface of the sleeve 38Ac, from which the distal-end electrode 27 extends, such that the distal end surface is in tight contact with the outer surface of the distal-end electrode 27. An opening 38B is formed on the lower portion, as viewed in the figure, of the distal end of each sleeve 38Ac. Thus, air expelled from the openings of the distal ends of the sleeves 38Ac is ejected along the distal-end electrode 27 in a manner similar to the sleeves 38Aa shown in FIG. 10. Advantageously, bubbles to cover the whole periphery of the distal-end electrode 27 can be efficiently generated in a shorter time.

FIG. 14 shows a modification of the distal-end electrode 27. The distal-end electrode 27 may be a metal tube with a plurality of holes 27a, which are formed in a portion exposed from the distal ends of the sleeves 38. The outer surface of each proximal part of the distal-end electrode 27 is in airtight contact with the associated sleeve 38. Therefore, air supplied from the gas supply unit 70 to the electrode assembly 5 is expelled from the holes 27a of the distal-end electrode 27 through the inside thereof.

Thus, air expelled from the holes 27a of the distal-end electrode 27 becomes bubbles on the whole periphery of the distal-end electrode 27. Advantageously, the whole periphery of the distal-end electrode 27 is efficiently covered with bubbles.

In the use of any of the above-described sleeves 38Aa, 38Ab, and 38Ac shown in FIGS. 11 to 13 and the distal-end electrode 27 with the holes 27a shown in FIG. 14, electric discharge to the insertion section 6 from the distal-end electrode 27 in contact with body tissue can be easily generated in a short time and the above-described similar advantages can be obtained.

Third Embodiment

A third embodiment will now be described with reference to FIGS. 15 and 16.

Figure 15:
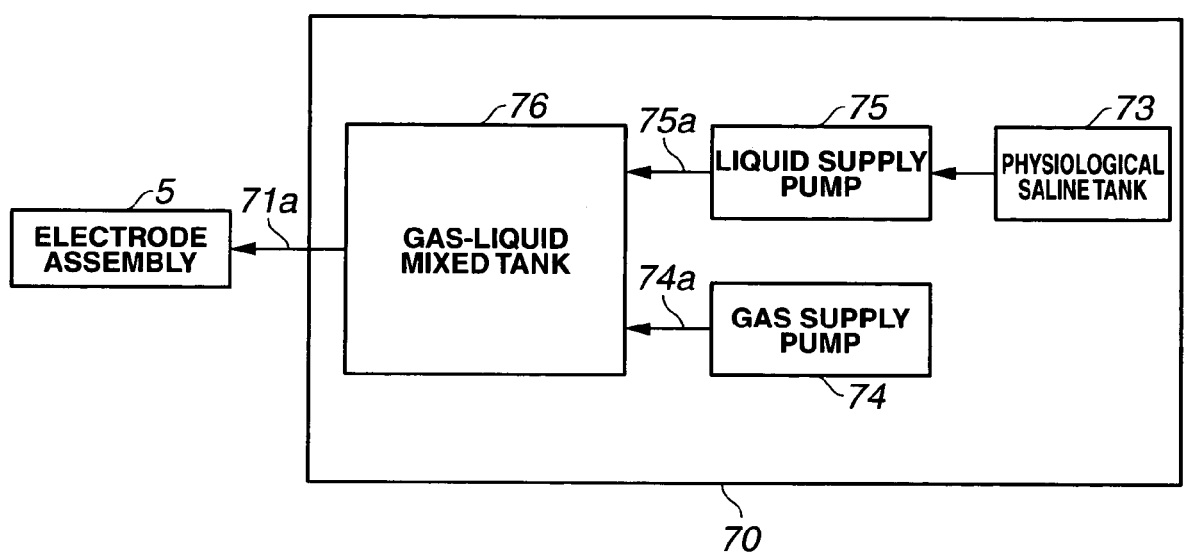
FIG. 15 is a block diagram showing an electrode assembly and a gas supply unit according to a third embodiment.
Figure 16:
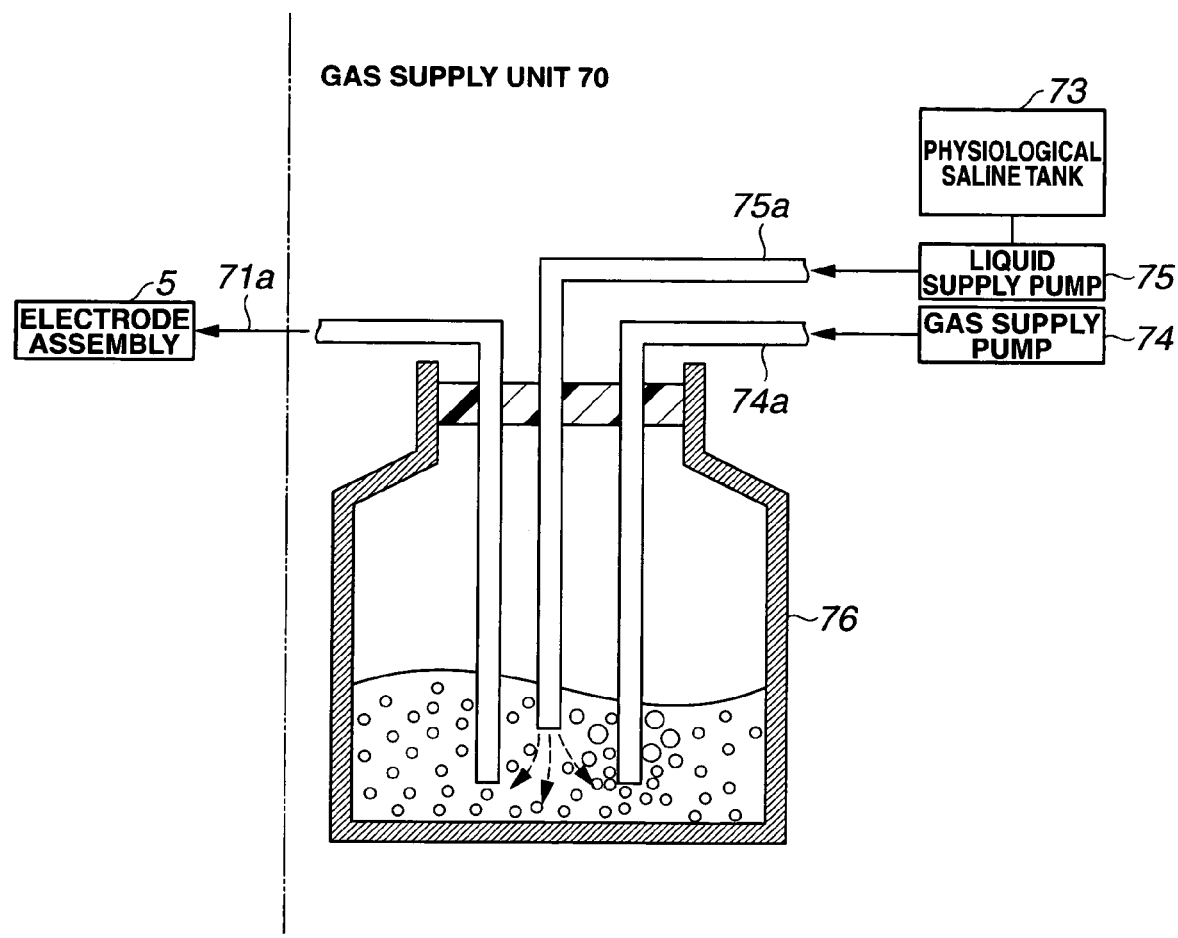
FIG. 16 is a diagram explaining the operation of a gas-liquid mixed tank of the gas supply unit according to the third embodiment.

FIGS. 15 and 16 relate to the third embodiment of the present invention. FIG. 15 is a block diagram showing an electrode assembly and a gas supply unit. FIG. 16 is a diagram explaining the operation of a gas-liquid mixed tank of the gas supply unit.

In the description of the present embodiment, the same components as those in the first and second embodiments are designated by the same reference numerals and a description of the previously described components is omitted.

Referring to FIG. 15, a gas supply unit 70 includes a physiological saline tank 73, a liquid supply pump 75 for sucking physiological saline in the physiological saline tank 73 and outputting the saline to a liquid supply pipe 75a, a gas supply pump 74 for outputting air to a gas supply pipe 74a, and a gas-liquid mixed tank 76 connected to output terminals of the pipes 74a and 75a, respectively. In the present embodiment, the gas supply unit 70 serves as a gas-liquid mixed fluid supply unit.

Instead of the gas supply tube 71 according to the second embodiment, one end of a gas-liquid mixed tube 71a is connected to the gas-liquid mixed tank 76. The other end of the gas-liquid mixed tube 71a is connected to a gas supply connector 72 shown in FIG. 9 such that the gas-liquid mixed tube 71a communicates with an inner duct of an electrode assembly 5.

As shown in FIG. 16, in the gas supply unit 70 with the above-described structure, the gas-liquid mixed tank 76 is supplied with physiological saline, output from the physiological saline tank 73 to the liquid supply pipe 75a by the liquid supply pump 75, and is also supplied with air output to the gas supply pipe 74a by the gas supply pump 74. In the gas-liquid mixed tank 76, therefore, physiological saline and air are mixed to produce a gas-mixed liquid.

The gas-liquid mixed tank 76 includes a lid so as to hermetically seal the tank. The respective pipes 74a and 75a and the gas-liquid mixed tube 71a extend through the lid of the gas-liquid mixed tank 76 such that the outer surfaces of the pipes and the tube are in tight contact with the lid.

Therefore, the pressure in the gas-liquid mixed tank 76 is increased by supplied physiological saline and air, so that the gas-mixed liquid produced in the gas-liquid mixed tank 76 is output to the gas-liquid mixed tube 71a and is then supplied to the electrode assembly 5.

Thus, the gas-mixed liquid is allowed to flow in the distal end of the electrode assembly 5 and is then expelled from openings at the distal ends of sleeves 38 to cover the whole periphery of a distal-end electrode 27.

Advantageously, in addition to the advantages of the first and second embodiments, electric discharge to an insertion section 6 from the distal-end electrode 27 in contact with body tissue can be easily generated using the gas-mixed liquid, i.e., an air-mixed liquid in a short time with higher efficiency.

Fourth Embodiment

A fourth embodiment will now be described below with reference to FIGS. 17 to 20.

Figure 17:
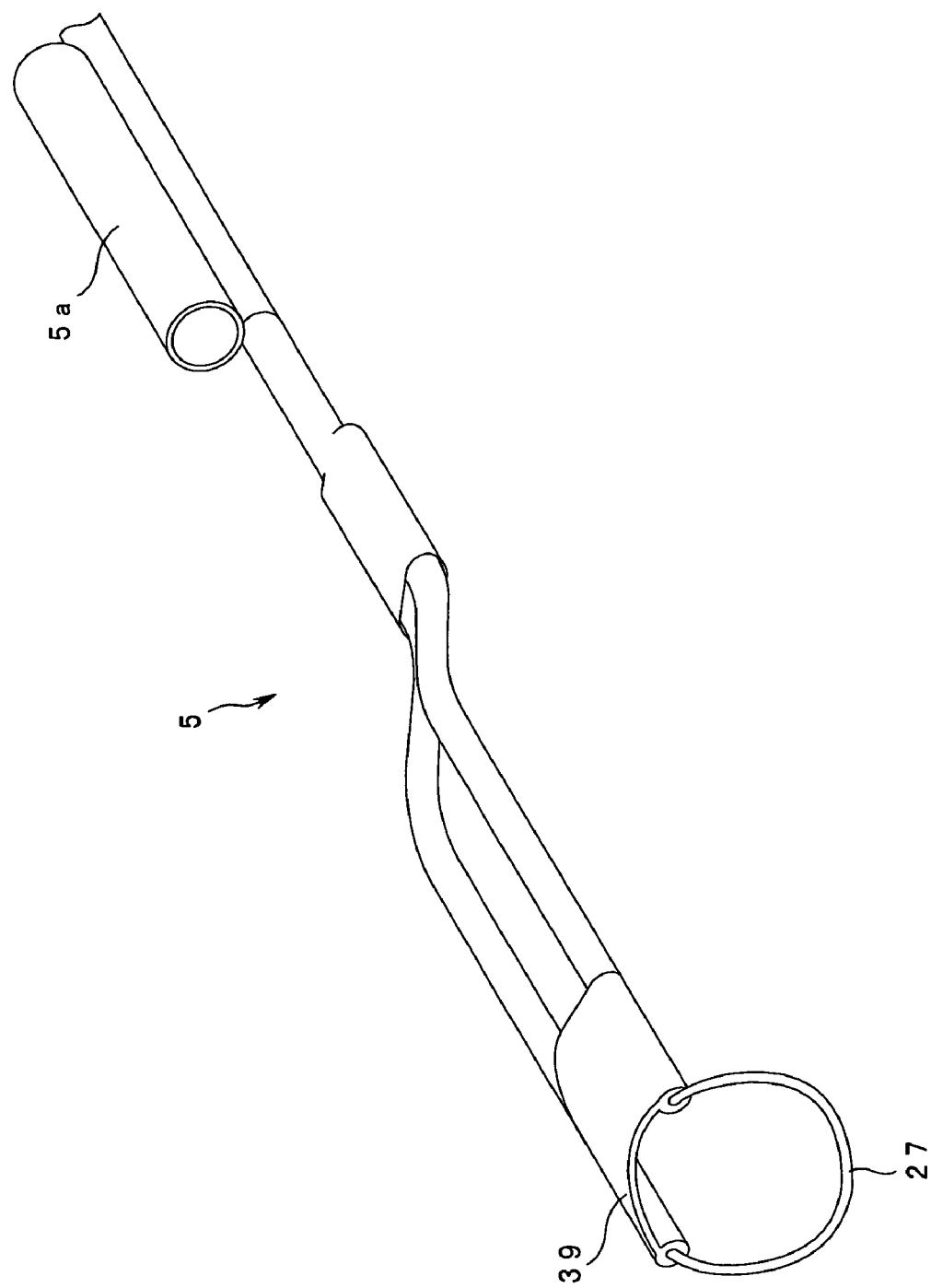
FIG. 17 is a diagram of the structure of an electrode assembly according to a fourth embodiment.
Figure 18:
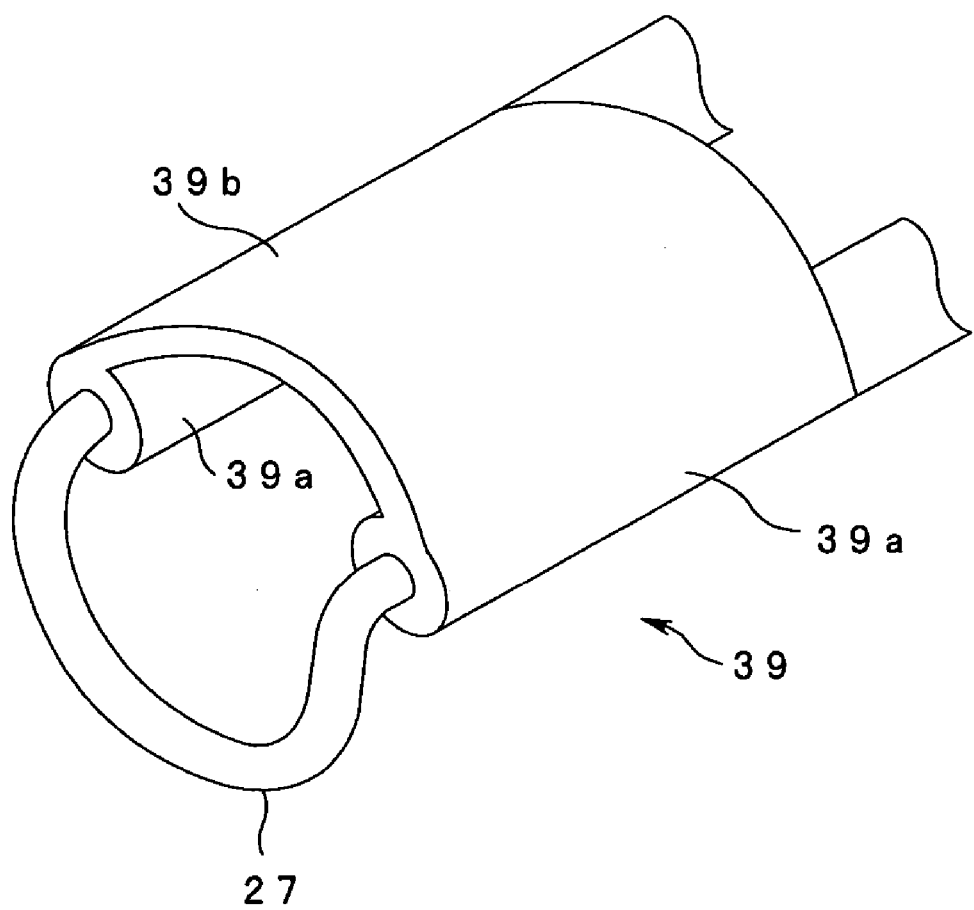
FIG. 18 is an enlarged view of distal end part of the electrode assembly according to the fourth embodiment.
Figure 19:
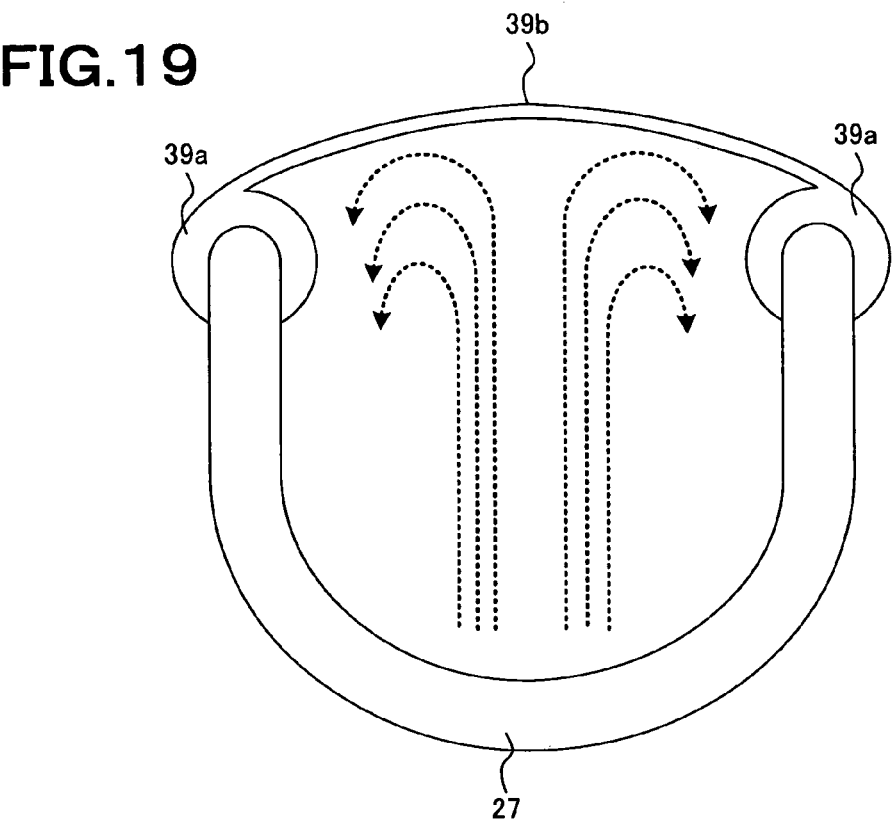
FIG. 19 is a front view of the electrode assembly as viewed from the front side to explain the operation thereof according to the fourth embodiment.
Figure 20:
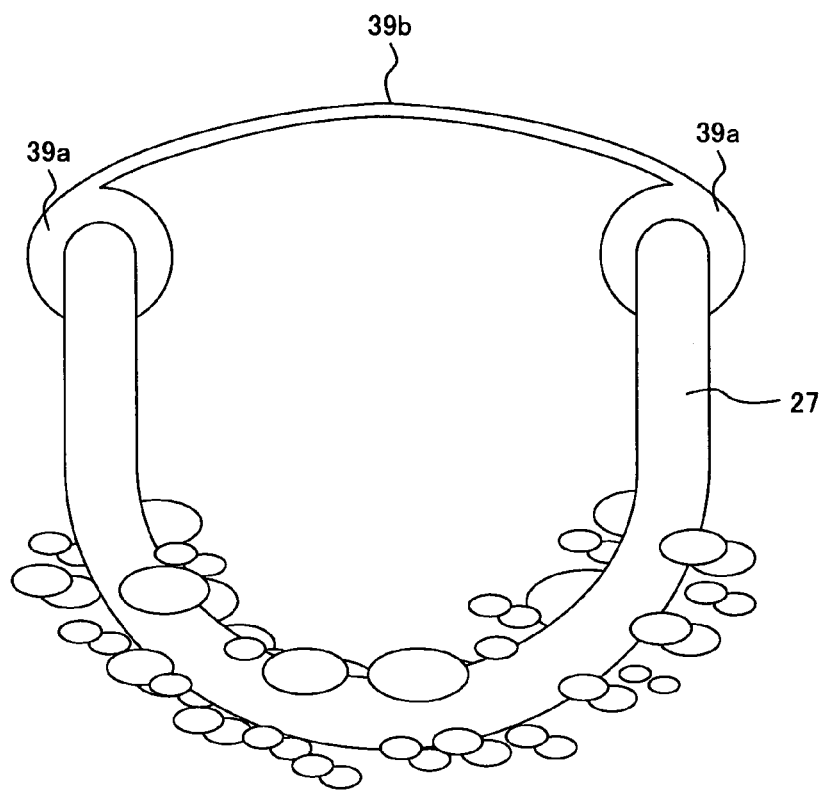
FIG. 20 is a front view of the electrode assembly as viewed from the front side to explain the operation thereof according to the fourth embodiment.

FIGS. 17 to 20 relate to the fourth embodiment of the present invention. FIG. 17 is a diagram of the structure of an electrode assembly. FIG. 18 is an enlarged view of distal end part of the electrode assembly. FIGS. 19 and 20 are enlarged views of distal part of a resectoscope to explain the operation thereof. In the description of the present embodiment, the same components as those of the first to third embodiments are designated by the same reference numerals and a description thereof is omitted.

Referring to FIG. 17, a band-shaped member 39, serving as a retaining mechanism, made of an electric insulating material is attached to the distal ends of branched parts of an electrode assembly 5. Specifically, in the electrode assembly 5, two metallic lines extend between a distal-end electrode 27 and a branch point adjacent to the proximal end such that the longitudinal axes of the lines are substantially parallel to each other. The band-shaped member 39 constituting the retaining mechanism is stretched between the two metallic lines such as to cover parts of the metallic lines, the covered parts being adjacent to the distal-end electrode 27.

Referring to FIG. 18, the band-shaped member 39, arranged at the distal end part of the electrode assembly 5, includes two cover segments 39a positioned on both sides in the sliding direction and a curved band segment 39b, serving as upper part of the member 39. The cover segments 39a partially cover the two metallic lines which extend from the distal-end electrode 27 to the proximal end, respectively. The band segment 39b is convex in cross section and interconnects the upper sides of the two cover segments 39a. In other words, since the band segment 39b of the band-shaped member 39 is arranged between the two metallic lines in the vicinity of the upper side of the distal-end electrode 27 formed in a substantially loop shape, the electrode assembly 5 seems to be partially covered by a curved plate.

The operation of a resectoscope with the above-described structure, serving as a high-frequency treatment apparatus, according to the present embodiment will now be described with reference to the above-described flowchart of FIG. 7 and FIGS. 19 and 20.

First, a resectoscope 1 is inserted into the body cavity of a patient through the urethra or vagina thereof. A high-frequency generation circuit 52 is controlled in accordance with steps S1 to S3 in FIG. 7, thus starting the supply of a high-frequency current output.

Specifically, upward convection occurs in physiological saline heated by a high-frequency current remaining in the vicinity of the distal-end electrode 27. In other words, as the temperature of physiological saline surrounding the distal-end electrode 27 is higher, the density of physiological saline is lower due to expansion. Lower-temperature surrounding physiological saline flows into the higher-temperature physiological saline. Such a phenomenon is repeated, so that the higher-temperature physiological saline ascends.

For part of the ascending physiological saline, as shown in FIG. 19, the band segment 39b of the band-shaped member 39 blocks the upward convection, thus causing a flow shown by arrows in the drawing. In other words, the ascending physiological saline hits against the band segment 39b of the band-shaped member 39, thus downwardly deflecting the flow toward the distal-end electrode 27 located on the lower side. Consequently, the convection of physiological saline occurs in the vicinity of the distal-end electrode 27, heat is transferred from the distal-end electrode 27 to physiological saline, and the temperature of physiological saline is increased to the temperature at which bubbles are generated in a short time. As shown in FIG. 20, bubbles are easily generated on the periphery of the distal-end electrode 27.

Therefore, the whole periphery of the distal-end electrode 27 can be covered with generated bubbles within a short time. Thus, the high-frequency current supplied to the distal-end electrode 27 is efficiently discharged from an area where the distal-end electrode 27 is in contact with body tissue to the insertion section 6.

In other words, the high-frequency current, supplied to the distal-end electrode 27, flows from an area where the distal-end electrode 27, serving as a current-applying electrode, is in contact with body tissue to the insertion section 6 located on the return side. Consequently, the body tissue in contact with the distal-end electrode 27 is subjected to resection, vaporization, or electric coagulation.

As compared with the electrode 912 provided for the conventional resectoscope apparatus 901 shown in FIGS. 30 to 32, the resectoscope 1 according to the present embodiment is designed so as to reduce the time required to generate bubbles to cover the whole periphery of the distal-end electrode 27 after the turn-on of a foot pedal of a footswitch 40.

Figure 21:
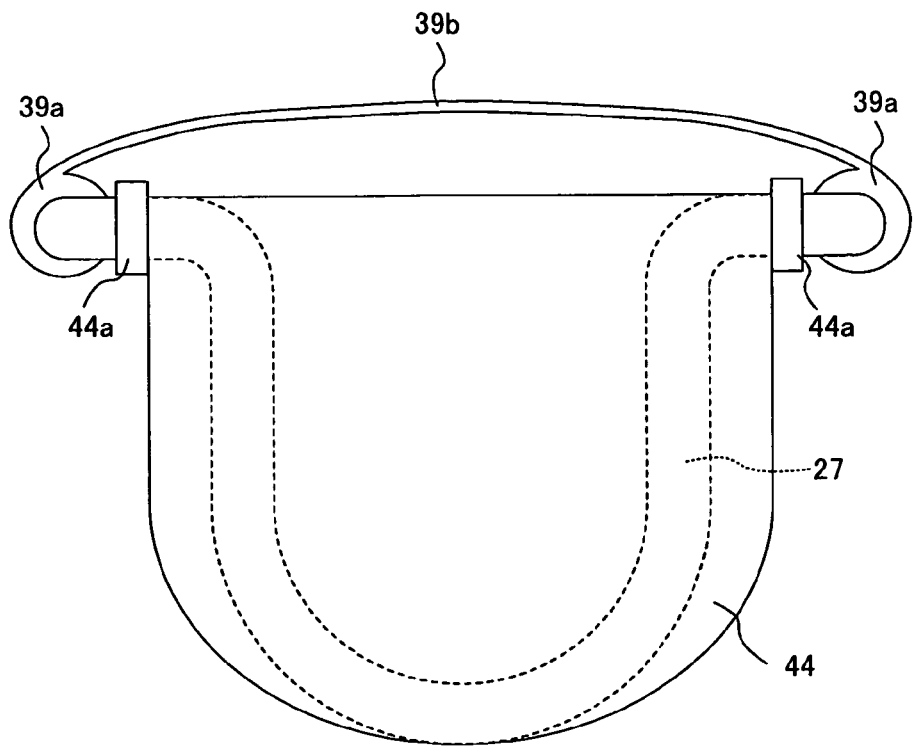
FIG. 21 is a front view of an electrode assembly according to a modification of the fourth embodiment as viewed from the front side.
Figure 22:
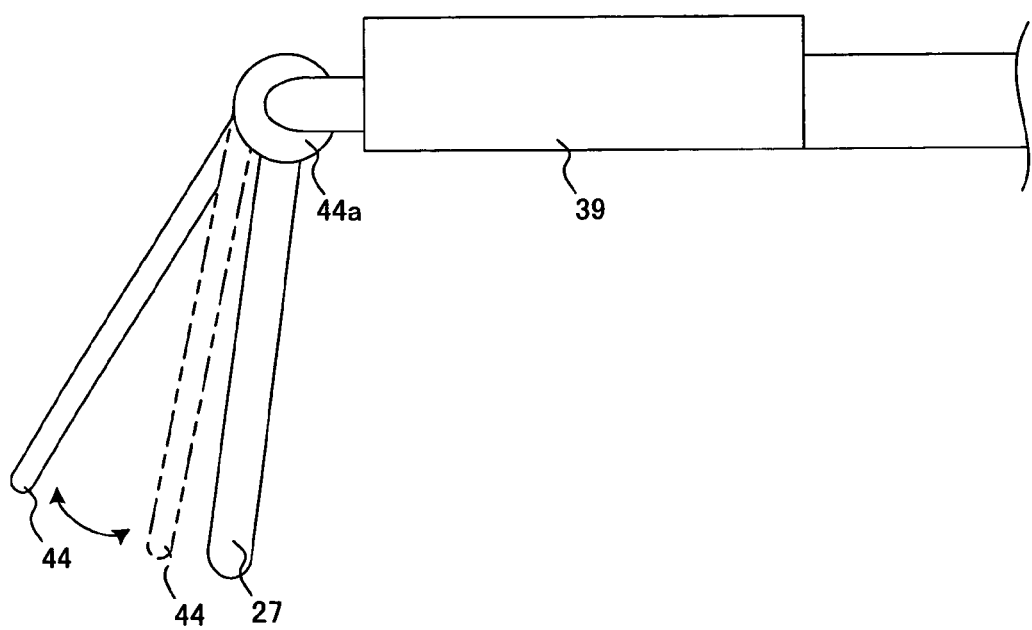
FIG. 22 is a side view of the distal end part of the electrode assembly according to the modification.

As shown in FIGS. 21 and 22, a plate 44, serving as a band-shaped member for a retaining mechanism, may be attached to the front side of the distal-end electrode 27 of the electrode assembly 5. FIG. 21 is a front view of an electrode assembly with a plate according to a modification of the present embodiment. FIG. 22 is a side view of the distal end of the electrode assembly.

More specifically, the pivotable plate 44, serving as a band-shaped member, made of a non-metallic material is attached to the distal end of an electrode assembly 5 through ring-shaped holders 44a. The holders 44a are arranged in respective exposed base parts of a distal-end electrode 27.

According to the modification, the distal-end electrode 27 is shaped as follows so that the holders 44a for the plate 44 can be attached to the exposed base parts thereof. The base parts of the distal-end electrode 27 are projected from the band-shaped member 39 and are bent inward and are then bent downward such as to form a loop.

The plate 44 covers the front surface of the distal-end electrode 27. The plate 44 is pivotable about the axis of each exposed base part of the distal-end electrode 27 through the corresponding holder 44a. In normal times, the plate 44 is in contact with the distal-end electrode 27 due to its own weight.

During resection, vaporization, or electric coagulation of body tissue, the electrode assembly 5 is slid toward the proximal end. At that time, the lower edge of the plate 44 is caught in body tissue, so that the plate 44 is pivoted away from the distal-end electrode 27. In other words, the angle formed between one plane of the plate 44 and an axis perpendicular to the direction in which the insertion section 6 is inserted is changed by pivoting of the plate 44.

With this arrangement, physiological saline, heated in the vicinity of the distal-end electrode 27, flowing to the distal end of the electrode assembly 5 is blocked by the plate 44, so that the heated physiological saline is retained in the vicinity of the distal-end electrode 27. Consequently, the temperature of heated physiological saline can be increased to the temperature required to generate bubbles from the distal-end electrode 27 with higher efficiency by the change of convection through the band segment 39b of the band-shaped member 39 arranged above the distal-end electrode 27 and the blocking of the forward flow of physiological saline from the electrode assembly 5 by means of the plate 44.

The band-shaped member 39 may be omitted in the electrode assembly 5. The plate 44 alone may be attached to the distal-end electrode 27.

Fifth Embodiment

A fifth embodiment will now be described below with reference to FIGS. 23 to 27.

Figure 23:
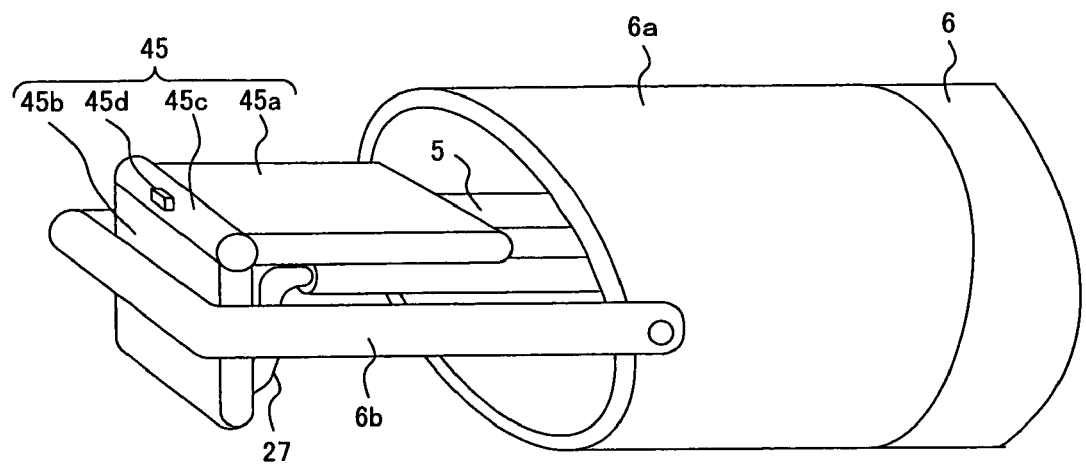
FIG. 23 is a diagram showing the structure of distal end part of a resectoscope according to a fifth embodiment.
Figure 24:
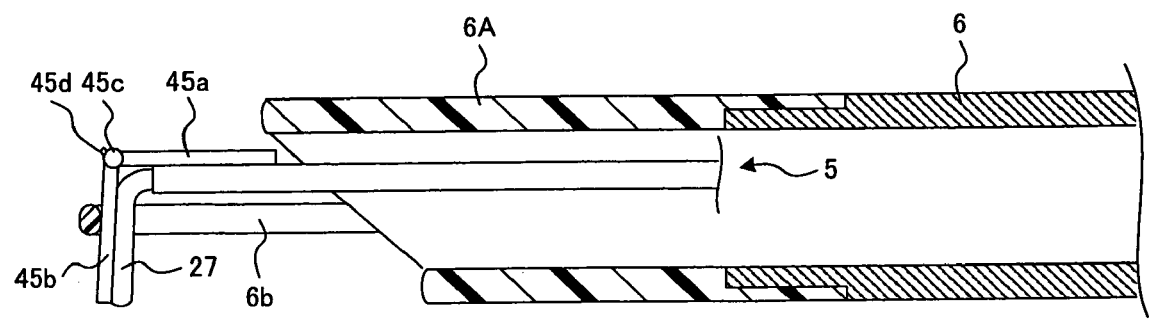
FIG. 24 is a sectional view of the distal end part of the resectoscope according to the fifth embodiment.
Figure 25:
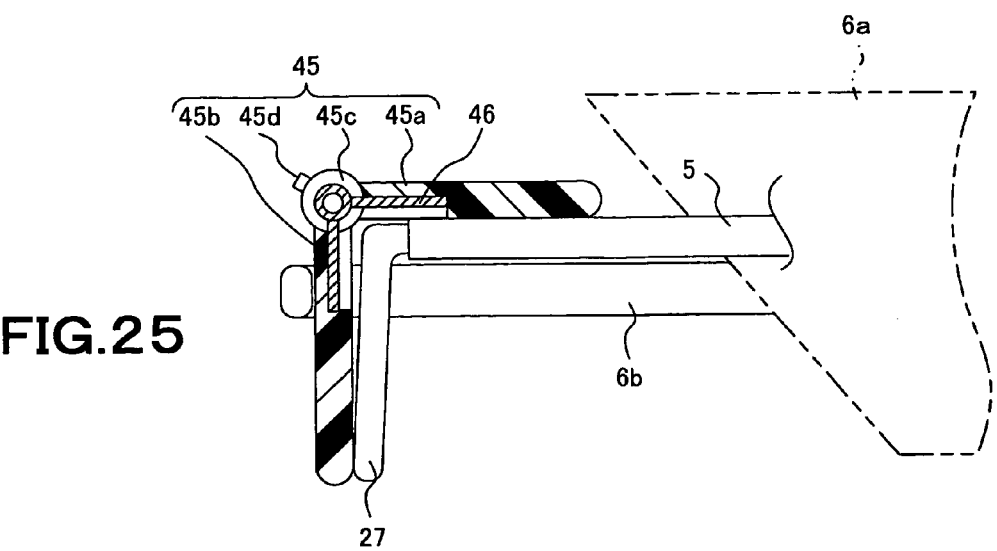
FIG. 25 is a sectional view of the distal end part of the resectoscope to explain the operation according to the fifth embodiment.
Figure 26:
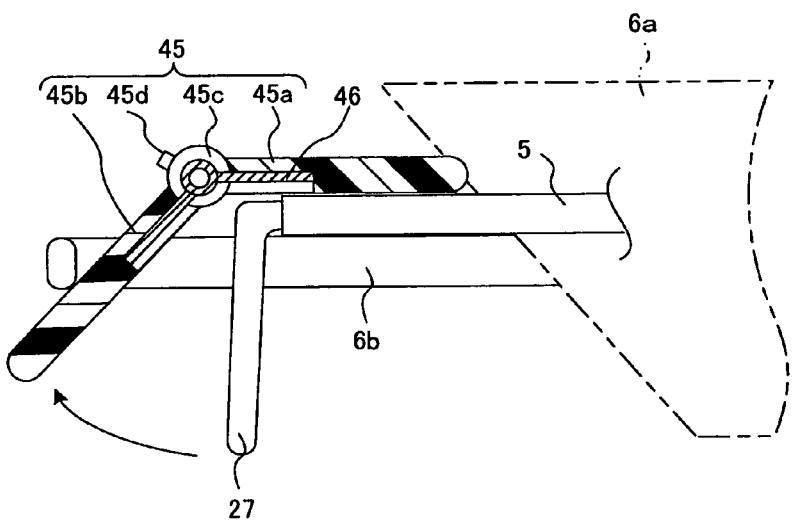
FIG. 26 is a sectional view of the distal end part of the resectoscope to explain the operation according to the fifth embodiment.
Figure 27:
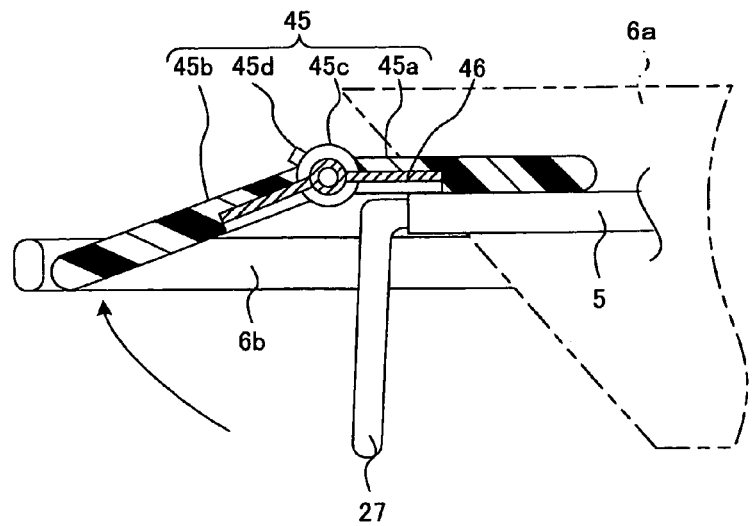
FIG. 27 is a sectional view of the distal end part of the resectoscope to explain the operation according to the fifth embodiment.

FIGS. 23 to 27 relate to the fifth embodiment of the present invention. FIG. 23 is a diagram showing the structure of distal end part of a resectoscope. FIG. 24 is a sectional view of the distal end part of the resectoscope. FIGS. 25 to 27 are sectional view of the distal end part of the resectoscope to explain the operation thereof.

In the description of the present embodiment, the same components as those in the above-described embodiments are designated by the same reference numerals and a description of the previously described components is omitted.

Referring to FIGS. 23 and 24, a distal end stopper 6b formed in a substantially U-shape so as to surround an opening of a distal end portion 6a is fixed to a resectoscope 1 according to the present embodiment. The distal end stopper 6b, made of a metallic material coated with plastic or insulating material, is fixed to both sides of the distal end portion 6a.

The longitudinal axis of the distal end stopper 6b is parallel to the longitudinal axis of an insertion section 6 of the resectoscope 1. The distal end stopper 6b is fixed to the distal end portion 6a such that side segments constituting the substantially U-shape are positioned in a plane that makes a substantially right angle with the vertical direction.

According to the present embodiment, an electrode assembly 5 includes a plate 45, serving as a band-shaped member for a retaining mechanism, for covering the front side (distal end) of a distal-end electrode 27 and the upper side of the distal end part of the electrode assembly 5. The plate 45 includes an upper plate segment 45a for covering the upper side of the distal end part of the electrode assembly 5, a front (distal end) plate segment 45b for covering the front side of the distal-end electrode 27, and a hinge 45c that interconnects the upper plate segment 45a and the front plate segment 45b.

The hinge 45c rotatably supports the front plate segment 45b. A stopper 45d for restricting the pivoting of the front plate segment 45b is arranged in substantially the middle of the upper surface of the hinge 45c. The upper plate segment 45a is secured to the upper side of the distal end part of the electrode assembly 5. As shown in FIGS. 25 to 27, a torsion coil spring 46 is loaded in the plate 45. The torsion coil spring 46 upwardly biases the front plate segment 45b pivotable about the hinge 45c.

In the plate 45, the angle which one plane of the upper plate segment 45a forms with an axis substantially orthogonal to the longitudinal axis of the insertion section 6 is substantially 90°. The angle which one plane of the front plate segment 45b, pivoted by the hinge 45c, forms with the axis perpendicular to the longitudinal axis of the insertion section 6 depends on sliding of the electrode assembly 5.

The operation of the resectoscope 1 with the above-described structure according to the present embodiment will now be described with reference to FIGS. 25 to 27.

To perform resection, vaporization, or electric coagulation of body tissue, an operator first slides the electrode assembly 5 so that the electrode assembly 5 is projected forward from the distal end portion 6a of the insertion section 6. At that time, the plate 45 is projected forward together with the electrode assembly 5 and the front plate segment 45*b* is come into contact with the distal end stopper 6*b*.

As shown in FIG. 25, the front plate segment 45*b* is come into contact with the distal end stopper 6*b* and the distal-end electrode 27. Both surfaces of the plate segment are oriented substantially vertically, so that forward sliding of the electrode assembly 5 is restricted. Under this condition, the operator turns on a foot pedal of a footswitch 40 (see FIG. 1) to supply a high-frequency current to the electrode assembly 5.

For physiological saline in the vicinity of the distal-end electrode 27 of the electrode assembly 5, when the temperature of physiological saline is increased, upward convection occurs. In this instance, the plate 45 covering the front and upper sides of the distal-end electrode 27 cause the convection of physiological saline in the vicinity of the distal-end electrode 27 to transfer heat generated from the distal-end electrode 27 to physiological saline, so that the temperature of physiological saline is increased to the temperature required to generate bubbles in a short time. Thus, bubbles are easily generated from the periphery of the distal-end electrode 27.

A high-frequency current, supplied to the distal-end electrode 27, flows from an area, where the distal-end electrode 27, serving as a current-applying electrode, is in contact with body tissue, to the insertion section 6 located on the return side. Consequently, the body tissue in contact with the distal-end electrode 27 is subjected to resection, vaporization, or electric coagulation. During surgical treatment of body tissue, e.g., resection, vaporization, or electric coagulation, the operator slides the electrode assembly 5 toward the proximal end.

At that time, as shown in FIG. 26, in the plate 45 moved together with the electrode assembly 5 toward the proximal end, the front plate segment 45*b* is pivoted upward about the axis of the hinge 45*c* by a biasing force of the torsion coil spring 46. The front plate segment 45*b* is pivoted such as to be gradually away from the distal-end electrode 27 while being in contact with the distal end stopper 6*b*.

Referring to FIG. 27, the stopper 45*d* of the hinge 45*c* blocks the front plate segment 45*b* from pivoting. The stopper 45*d* of the hinge 45*c* defines the blocking position of the pivoting front plate segment 45*b* to form a predetermined angle between the front plate segment 45*b* and the upper plate segment 45*a* so that when the front plate segment 45*b* is slid forward, part thereof is contactable with the distal end stopper 6*b*.

As described above, according to the present embodiment, in this arrangement in which the plate 45 for covering the vertical front and upper surfaces of the distal-end electrode 27 is provided for the electrode assembly 5 of the resectoscope 1, the same advantages as those of the fourth embodiment can be obtained.

Figure 28:
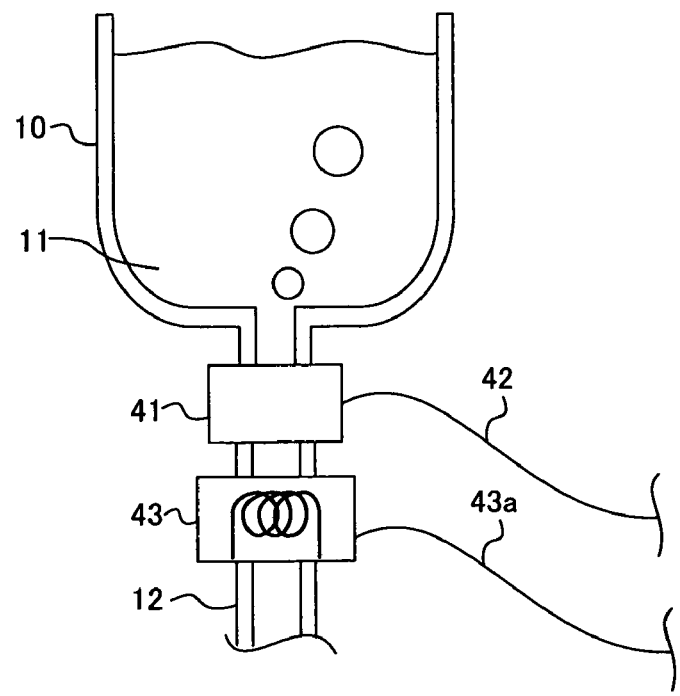
FIG. 28 is a diagram explaining a heater disposed in a liquid supply tube.
Figure 29:
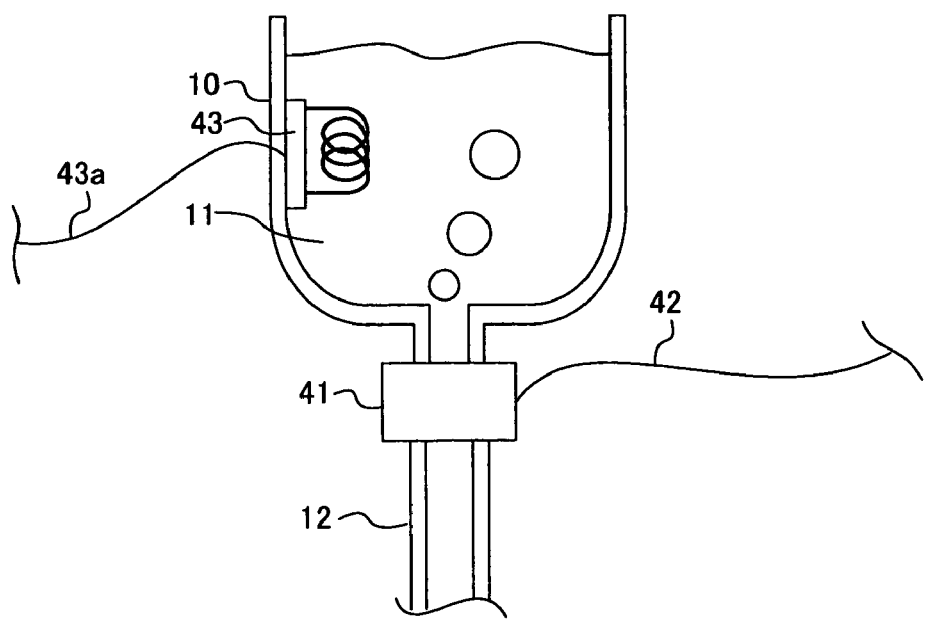
FIG. 29 is a diagram explaining the heater disposed in a pack.

In addition to the above-described embodiments, as shown in FIGS. 28 and 29, a heating unit for heating physiological saline may be provided for the pack 10 or the liquid supply tube 12 serving as a liquid supply unit shown in FIG. 1.

The heating unit includes a heater 43 having, e.g., a heating wire that generates heat. The heater 43 is supplied with electric power through an electric line 43*a*. The heater 43 may be interposed in the liquid supply tube 12 as shown in FIG. 28. Alternatively, the heater 43 may be disposed in the pack 10 as shown in FIG. 29.

The heater 43, supplied with electric power from the electric line, generates heat due to the impedance of the heating wire, thus heating physiological saline passing through the liquid supply tube 12 or held in the pack 10 to a predetermined temperature. Thus, the heated physiological saline is supplied into the body of a patient through the distal end portion 6*a* of the insertion section 6 of the resectoscope 1.

Since physiological saline has been heated at the predetermined temperature, the initial temperature of physiological saline supplied in the vicinity of the distal-end electrode 27 of the electrode assembly 5 is high. Thus, the time required to increase the temperature of physiological saline to the temperature at which bubbles are generated can be further reduced.

Therefore, providing the heater 43 leads to a reduction in time required to generate bubbles on the periphery of the distal-end electrode 27. Advantageously, since electric discharge between an area where the distal-end electrode 27 is in contact with body tissue and the insertion section 6 is effectively generated, the power consumption of the high-frequency power supply unit 21 can be reduced. In addition, high-frequency electric power to be used can be realized with a small amount of power.

In the resectoscope 1 according to each of the above-described embodiments, the time required to cover the whole periphery of the distal-end electrode 27 with bubbles after starting of high-frequency current output by the high-frequency power supply unit 21 can be reduced, the covering with bubbles being needed to generate electric discharge between the distal-end electrode 27 and the insertion section 6. In other words, in the resectoscope 1 according to the present invention, with the arrangement such that the time required to increase the temperature of physiological saline in the vicinity of the distal-end electrode 27 can be reduced, alternatively, with the arrangement such that bubbles are forcedly generated in the vicinity of the distal-end electrode 27, it is possible to reduce time elapsed until electric discharge for resection, vaporization, or electric coagulation of body tissue is started.

Advantageously, in the resectoscope 1 according to the present invention, electric power saving effect can be obtained by reducing the time during which the high-frequency power supply unit 21 outputs a high-frequency current. Further, since bubbles in the vicinity of the distal-end electrode 27 are not scattered due to fluid supply, the whole of the distal-end electrode 27 is covered with bubbles to generate electric discharge by low electric power, so that resection, vaporization, or electric coagulation of body tissue can be achieved.

Consequently, the high-frequency power supply unit 21 with low electric power can be used. This leads to a reduction in manufacturing cost of the resectoscope 1, serving as a high-frequency treatment apparatus, and saving of electric power.

In the resectoscope 1 according to each of the above-described embodiments, bubbles are generated in the vicinity of the distal-end electrode 27 in a short time. Advantageously, since electric discharge between an area where the distal-end electrode 27 is in contact with body tissue and the insertion section 6 is effectively generated, the power consumption of the high-frequency power supply unit 21 can be reduced. In addition, high-frequency electric power to be used can be realized with a small amount of power.

Accordingly, an expensive high-frequency power supply unit 21 capable of outputting a large amount of power is not needed. An inexpensive high-frequency power supply unit 21 capable of immediately generating electric discharge between the distal-end electrode 27 and the insertion section 6 by a small amount of power while the distal-end electrode 27 is in contact with body tissue can be used. In the resectoscope 1 according to each of the above-described embodiments, since the time required to generate electric discharge can be reduced, the time required for surgical treatment can be reduced. Advantageously, burdens on a patient can also be reduced.

It should be understood that the present invention is not limited to the above-described embodiments and various changes and modifications thereof could be made without departing from the spirit or scope of the invention.

What is claimed is:

1. A high-frequency treatment apparatus comprising:
an electrode assembly electrically connected to a high-frequency generating unit for generating a high-frequency current, the assembly having, at the distal end thereof, a current-applying electrode for discharging the high-frequency current, the proximal end of the current-applying electrode being covered with an insulator;
an insertion section receiving the electrode assembly, the insertion section being located on the return side of the high-frequency current discharged from the current-applying electrode;
a liquid supply section for supplying an irrigation liquid to the vicinity of the current-applying electrode;
a pinch valve, disposed in a liquid supply path of the liquid supply section, for preventing a supply of irrigation liquid to a vicinity of the current-applying electrode when a calculated impedance between the current-applying electrode and the insertion section is less than a predetermined threshold value, and for resuming the supply of irrigation liquid when the calculated impedance is above the predetermined threshold value; and
a retaining mechanism, disposed in the vicinity of the current-applying electrode of the electrode assembly, for retaining the irrigation liquid, which is supplied by the liquid supply unit, the retaining mechanism is arranged rotatably with respect to the current-applying electrode, and the retaining mechanism includes a band-shaped member of which an angle formed relative to a longitudinal axis extending from a proximal end to a distal end of the insertion section varies according to an advance and retreat position of the current-applying electrode housed in the insertion section.

2. The apparatus according to claim 1, wherein the band-shaped member is arranged at the distal end of the current-applying electrode.

* * * * *